United States Patent
Kim et al.

(10) Patent No.: US 7,279,338 B2
(45) Date of Patent: Oct. 9, 2007

(54) METHODS FOR DETERMINING CELLULAR RESPONSE TO STIMULI

(75) Inventors: Chin Hong Paul Kim, Minneapolis, MN (US); John McDonald, Edina, MN (US); Sean S. Smith, Memphis, TN (US); Brian B. Anderson, Collierville, TN (US); Allen R. Muroski, Bartlett, TN (US); Brian Guthrie, Chanhassen, MN (US); Var Len St. Jeor, Lakeland, TN (US); John H. Teeter, Downington, PA (US); Nancy E. Rawson, Marlton, NJ (US)

(73) Assignee: Cargill, Incorporated, Wayzata, MN (US)

( * ) Notice: Subject to any disclaimer, the term of this patent is extended or adjusted under 35 U.S.C. 154(b) by 0 days.

(21) Appl. No.: 11/313,418

(22) Filed: Dec. 21, 2005

(65) Prior Publication Data

US 2006/0194261 A1    Aug. 31, 2006

Related U.S. Application Data

(60) Provisional application No. 60/639,152, filed on Dec. 22, 2004.

(51) Int. Cl.
*G01N 1/18* (2006.01)

(52) U.S. Cl. .................. 436/177; 436/56; 436/149; 435/4; 435/7.2

(58) Field of Classification Search ............... 436/164, 436/56, 149, 177; 435/4, 7.2
See application file for complete search history.

(56) References Cited

U.S. PATENT DOCUMENTS

| | | |
|---|---|---|
| 6,818,747 B2 | 11/2004 | Yao et al. |
| 6,955,887 B2 | 10/2005 | Adler et al. |
| 7,022,488 B2 | 4/2006 | Servant et al. |
| 7,041,457 B2 | 5/2006 | Yao et al. |
| 7,052,857 B2 | 5/2006 | Zoller et al. |
| 2002/0128433 A1 | 9/2002 | Yao et al. |
| 2002/0132273 A1 | 9/2002 | Stryer et al. |
| 2002/0143151 A1 | 10/2002 | Yao et al. |
| 2003/0040045 A1 | 2/2003 | Zuker et al. |
| 2003/0054448 A1 | 3/2003 | Adler et al. |
| 2003/0089885 A1 | 5/2003 | Rogers et al. |
| 2003/0170608 A1 | 9/2003 | Pronin et al. |
| 2003/0207337 A1 | 11/2003 | Han et al. |
| 2003/0220479 A1 | 11/2003 | Li et al. |
| 2003/0228633 A1 | 12/2003 | Zoller et al. |
| 2003/0232407 A1 | 12/2003 | Zoller et al. |
| 2004/0072254 A1 | 4/2004 | Callamaras et al. |
| 2004/0132075 A1 | 7/2004 | Elliot et al. |
| 2004/0132134 A1 | 7/2004 | Adler et al. |
| 2004/0171042 A1 | 9/2004 | Adler et al. |
| 2004/0175792 A1 | 9/2004 | Zoller et al. |
| 2004/0175793 A1 | 9/2004 | Zoller et al. |
| 2004/0185469 A1 | 9/2004 | Zoller et al. |
| 2004/0191805 A1 | 9/2004 | Adler et al. |
| 2004/0191862 A1 | 9/2004 | Zoller et al. |
| 2004/0209286 A1 | 10/2004 | Adler et al. |
| 2004/0214239 A1 | 10/2004 | Servant et al. |
| 2004/0229239 A1 | 11/2004 | Adler et al. |
| 2005/0032158 A1 | 2/2005 | Adler et al. |
| 2005/0033021 A1 | 2/2005 | Li et al. |
| 2005/0069944 A1 | 3/2005 | Adler |
| 2005/0084506 A1 | 4/2005 | Tachdjian et al. |
| 2005/0084932 A1 | 4/2005 | Zoller et al. |
| 2005/0085625 A1 | 4/2005 | Li et al. |
| 2005/0136512 A1 | 6/2005 | Yao et al. |
| 2005/0233383 A1 | 10/2005 | Zozulya |
| 2005/0287517 A1 | 12/2005 | Adler et al. |
| 2006/0014208 A1 | 1/2006 | Zoller et al. |
| 2006/0019346 A1 | 1/2006 | Xu et al. |
| 2006/0084117 A1 | 4/2006 | Yao et al. |

OTHER PUBLICATIONS

Caicedo et al. Science 2001 vol. 291, pp. 1557-1560.*
Tonosaki et al. Comp. Biochem. Physiol. 1984 vol. 79A, pp. 625-630.*
Max et al. Nature Genetics 2001 vol. 28, pp. 58-63.*
Witt et al. (Anat. Rec. 1996 vol. 246, pp. 507-523.*
Blatt MR, Slayman CL. KCl leakage from microelectrodes and its impact on the membrane parameters of a nonexcitable cell. J Membr Biol. 1983; 72(3):223-34.
Fahraeus C, Borglid K, Grampp W. Properties of electrolyte-filled glass microelectrodes: an experimental study. J Neurosci Methods. Dec. 30, 1997; 78(1-2):15-28.
Ince C, van Bavel E, van Duijn B, Donkersloot K, Coremans A, Ypey DL, Verveen AA. Intracellular microelectrode measurements in small cells evaluated with the patch clamp technique. Biophys J. Dec. 1986 50(6):1203-9.
Pelzer D, Trube G, Piper HM. Low resting potentials in single isolated heart cells due to membrane damage by the recording microelectrode. Pflugers Arch. Feb. 1984 400(2):197-9.
International Search Report for PCT/US05/41946 (2006).
International Search Report for PCT/US05/46339 (2006).
Ashworth, Approaches to measuring calcium in zebrafish: focus on neuronal development, Cell Calcium 35 (2004) 393-402.
Baryshnikov et al. 2003. Calcium signaling mediated by P2Y receptors in mouse taste cells. J. Neurophysiol. 90:3283-94.
Boudreau et al. 1973. Classification of chemoresponsive tongue units of the cat geniculate ganglion. Brain Res. 54:157-175.

(Continued)

*Primary Examiner*—Long V. Le
*Assistant Examiner*—Jacob Cheu
(74) *Attorney, Agent, or Firm*—Viksnins Harris & Padys PLLP; Edward L. Levine

(57) ABSTRACT

The present invention provides a method for determining cellular response to stimuli. The cells to be tested, for example, may be contained in a section of taste-bud containing lingual epithelium.

50 Claims, 12 Drawing Sheets
(8 of 12 Drawing Sheet(s) Filed in Color)

OTHER PUBLICATIONS

Boudreau et al. 1977. Chemical stimulus determinants of cat geniculate ganglion chemo-responsive group I discharge. Chem. Senses Flavour. 2:353-374.

Boudreau et al. 1971. Single unit recordings from the geniculate ganglion of the facial nerve of the cat. Exp. Brain Res. 13:461-488.

Boudreau et al. 1985. Neurophysiology of geniculate ganglion (facial nerve) taste systems: species comparisons. Chem. Senses. 10:89-127.

Bourne et al. 1999. Co-localization of serotonin-like immunoreactivity with synaptic proteins in taste buds of rat. Chem. Senses. 24:589.

Brand et al. 1991. Transduction mechanism for the taste of amino acids. Physiol. Behav. 49: 899-904.

Caicedo et al. Taste receptor cells that discriminate between bitter stimuli. Science (2001) 291:1557-60.

Caicedo et al. 2000. In Situ Ca Imaging Reveals Neurotransmitter Receptors for Glutamate in Taste Receptor Cells. The Journal of Neuroscience, Nov. 1, 20(21):7978-7985.

Caicedo et al. 2002. Individual mouse taste cells respond to multiple chemical stimuli. J. Physiol. 544.2:501-509.

Caprio 1975. High sensitivity of catfish taste receptors to amino acids. Comp. Biochem. Physiol. A. 52:247-251.

Clapp et al. Immunocytochemical evidence for co-expression of Type III IP3 receptor with signaling components of bitter taste transduction, BMC Neurosci., 2:6 (2001).

Clapp,T.R. et al. 2003. Morphological characterization of rat taste receptor cells that express components of the pholpholipase C signaling pathway. J. Comp. Neurol. 468:311-321.

Danilova et al. 1999. Responses of single taste fibers and whole chorda tympani and glossopharyngeal nerve in the domestic pig, Sus scrofa. Chemical Senses, 24:301-316.

Delay et al. 1986. Ultrastructure of mouse vallate taste buds. II. Cell types and cell lineage. J. Comp. Neurol. 253:242-252.

Finger et al. 1996. Differential localization of putative amino acid receptors in taste buds of the channel catfish, Ictalurus punctatus. Journal of Comparative Neurology. 373: 129-138.

Finger, T.E. and S.A. Simon. 2000. Cell biology of taste epithelium. In: *The Neurobiology of Taste and Smell*, 2nd Edition., New York, Wiley-Liss. Finger, T.E., Silver, W.L. and Restrepo, D., eds. pp. 287-314.

Finger et al., "ATP signaling is crucial for communication from taste buds to gustatory nerves", Science, 310(5753), 1495-1499 (2005).

Fugimoto et al. 1987 Immunocytochemistry on the localization of 5-hydroxytryptamine in monkey and rabbit taste buds. Acta Anat. (Basel). 128-80-83.

Gratton et al. 2003. Fluorescence lifetime imaging for the two-photon microscope: time-domain and frequency-domain methods. J. Biomed. Optics. 8:381-390.

Hayashi et al. 1996. Measurement of membrane potential and $[Ca^{2+}]_i$ in cell ensembles: Application to the study of glutamate taste in mice. Biophysical Journal. 71:1057-1070.

He et al. 2002. Partial rescue of taste responses of alpha-gustducin in null mice by transgenic expression of alpha-transducin. Chemical Senses. 27:719-27.

Herness et al. 2005. Communication routes within the taste bud by neurotransmitters and neuropeptides. Chemical Senses. 30 Suppl. 1:i37-i38.

Kare, M.R., Pond, W.C., and Campbell, J., Eds. Observations on the taste reactions in pigs. In: *Animal Behaviour*, XIII, 2-3, 1965.

Kim et al. 1995. Localization of serotonin in taste buds: a comparative study of four vertebrates. J. Comp. Neurol. 353:364-370.

Kinnamon et al. 1985. Ultrastructure of mouse vallate taste buds. I. Taste cells and their associated synapses. J. Comp. Neurol. 235:48-60.

Kinnamon et al. 1988. Ultrastructure of mouse vallate taste buds. III. Patterns of synaptic connectivity. J. Comp. Neurol. 270:1-10.

Kinnamon et al. 1993. HVEM ultrastructural analysis of mouse fungiform taste buds, cell types, and associated synapses. Microsc. Res. Techniq. 26:142-156.

Koester et al. 1999. $Ca^{2+}$ fluorescence imaging with pico- and femtosecond two-photon excitation: signal and photodamage. Biophys. J. 77:2226-2236.

Konig et al. 1997. Cell damage in UVA and CW/femtosecond NIR microscopes. SPIE vol. 2983:37-44.

Krimm et al. 1998. Innervation of single fungiform taste buds during development in rat. J. Comp. Neurol. 398:13-24.

Kumazawa et al. 1990. Large synergism between monosodium glutamate and 5'-nucleotides in canine taste nerve responses. Am. J. Physiol. 259:R420-R426.

Kumazawa et al. 1990. Large enhancement of canine taste responses to sugars by salts. J. Gen. Physiol. 95:1007-1018.

Kumazawa et al. 1991. Canine taste nerve responses to umami substances. Physiol. Behav. 49:875-881.

Lindemann 1996. Taste reception, Physiol. Reviews, 76:718-766.

Liu et al. 2003. Intracellular $Ca^{2+}$ and the phospholipids $PIP_2$ regulate the taste transduction ion channel TRPM5. 2003. PNAS 100:15160-15165.

Lyall et al., "A Novel Vanilloid Receptor-1 (VR-1) Variant Mammalian Salt Taste Receptor", Chem Senses, 30 Suppl 1, i42-i43 (2005).

Lyall et al., 2004. The mammalian amiloride-insensitive non-specific salt taste receptor is a vanilloid receptor-1 variant. J Physiol. 558(Pt 1):147-59.

Medler et al. 2003. Electrophysiological characterization of voltage-gated currents in defined taste cell types of mice. J. Neurosci. 23:2608-2617.

Murray 1973. The ultrastructure of taste buds. In: *The Ultrastructure of Sensory Organs*. Friedemann, I., ed., Amsterdam. North Holland, pp. 1-81.

Nakamura et al. 1990. Non-specific inhibition by amiloride of canine chorda tympani nerve responses to various salts: do $Na^+$-specific channels exist in canine taste receptor membranes? Brain Res. 524:42-48.

Nakamura et al. 1991. Canine taste nerve responses to monosodium glutamate and disodium guanylate: differentiation between umami and salt components with amiloride. Brain Res. 541:21-28.

Nelson et al. 1993. Immunolocalization of different forms of neural cell adhesion molecule (NCAM) in rat taste buds. J. Comp. Neurol. 336:507-516.

Pelet et al. P.T.C. A Fast Global Fitting Algorithm for Fluorescence Lifetime Imaging Microscopy Based on Image Segmentation. 2004. Biophysical Journal 87: 2807-2817.

Reutter 1971. Die Geschmacksknospen des Zwergwelses Ameiurus nebulosus. Morphologischische and histochemische Untersuchungen. Z. Zellforsch. 120:280-308. (English Summary).

Reutter et al. 1993. Morphology of vertebrate taste organs and their nerve supply. In: *Mechanisms of Taste Transduction*. Simon, S.A. and Roper, S.D., eds. Boca Raton, FL. CRC Press, pp. 29-52.

Richter et al. Sour taste stimuli evoke $Ca^{+2}$ and pH responses in mouse taste cells. J. of Physiology (2003) 547:475-83.

Roper 1989. The Cell Biology of Vertebrate Taste Receptors. Ann. Rev. Neurosci. 12:329-353.

Royer et al. 1991. HVEM serial-section analysis of rabbit foliate taste buds: I. Type III cells and their synapses. J Comp Neurol. 306(1):49-72.

Royer et al. 1994. Application of serial sectioning and three dimensional reconstruction to the study of taste bud ultrastructure and organization. Microsc. Res. Techniq. 29:381-407.

Takeda et al. 1975. Fine structure of taste buds in the rat. Arch. Histol. Jpn. 37:395-413.

Tonosaki 1984. The mouse taste cell response to five sugar stimuli. Comp. Biochem. Physiol. 79A(4):625-630.

Uchida 1985. Serotonin-like immunoreactivity in the taste bud of the mouse circumvallate papilla. Jpn. J. Oral Biol. 27:132-139. (English Abstract).

Witt et al. 1996. Embryonic and early fetal development of human taste buds: a transmission electron microscopical study. Anat Rec. 246(4):507-23.

Yang et al. 2000. Taste bud cells with synapses express SNAP-25-like immunoreactivity. J.Comp. Neurol. 424A:205-215.

Yang et al. 2004. Synpatobrevin-2-like immunoreactivity is associated with vesicles at synapses in rat circumvallate taste buds. J. Comp. Neurol. 47:59-71.

Yee et al. 2001. "Type III" cells of rat taste buds: immunohistochemical and ultrastructural studies of neuron-specific enolase, protein gene product 9.5, and serotonin. J. Comp. Neurol. 440:97-108.

Yee et al. 2003. Brain-derived neurotrophic factor is present in adult mouse taste cells with synapses. J. Comp. Neurol. 459:15-24.

Zviman et al. 1996. Single taste stimuli elicit either increases or decreases in intracellular calcium in isolated catfish taste cells. J. of Membrane Biology 149:81-88.

* cited by examiner

Fig. 4A
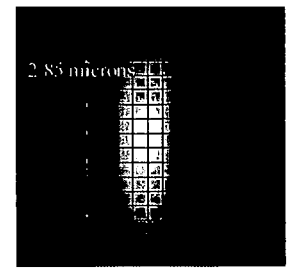
Fig. 4C
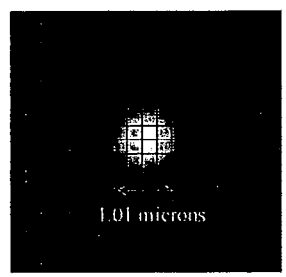
Fig. 4B
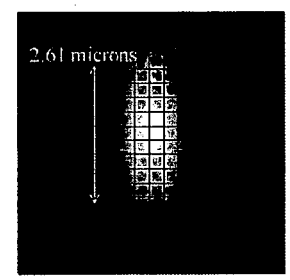
Fig. 4D
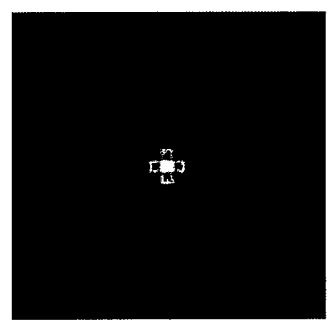
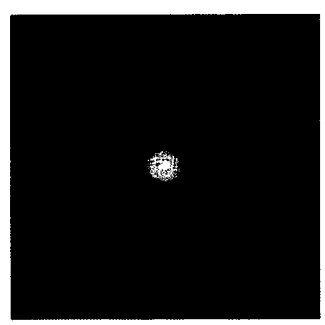
Fig. 5A       Fig. 5B

METHODS FOR DETERMINING CELLULAR RESPONSE TO STIMULI

RELATED APPLICATION

This patent document claims the benefit of priority of U.S. application Ser. No. 60/639,152, filed Dec. 22, 2004, and PCT application number PCT/US2005/41946 filed on Nov. 17, 2005, which applications are herein incorporated by reference.

BACKGROUND OF THE INVENTION

Taste transduction is one of the most sophisticated forms of chemotransduction in animals. Gustatory signaling is found throughout the animal kingdom, from simple metazoans to the most complex vertebrates. Its main purpose is to provide a reliable signaling response to non-volatile ligands. Humans typically distinguish several perceptual taste qualities or modalities: sweet, sour, salty, bitter and umami. Each of these modalities is thought to be mediated by distinct signaling pathways mediated by receptors or channels, leading to receptor cell depolarization, generation of a receptor or action potential, and release of neurotransmitter at gustatory afferent neuron synapses.

Taste transduction in animals is mediated by specialized neuroepithelial cells, referred to as taste receptor cells. These cells are organized into groups of about 40 to 100 cells to form taste buds. Taste buds contain precursor cells, support cells, and taste receptor cells. Receptor cells are innervated at their base by afferent nerve endings that transmit information to the taste centers of the cortex through synapses in the brain stem and thalamus. Taste buds are distributed into different papillae in the tongue epithelium. Circumvallate papillae, found at the very back of the tongue, contain hundreds to thousands of taste buds. By contrast, foliate papillae, localized to the posterior lateral edge of the tongue, contain dozens to hundreds of taste buds. Further, fungiform papillae, located on the anterior two-thirds of the tongue, contain only a single or few taste buds, depending upon the species. Taste cells are also found in the palate and other tissues, such as the esophagus and the stomach.

Taste buds are ovoid structures and are primarily embedded within the epithelium of the tongue. It is believed that taste transduction is initiated at the apical portion of a taste bud at the taste pore, where microvilli of the taste receptor cells make contact with the outside environment. Various taste stimulants cause either depolarization (i.e., a reduction in membrane potential) or hyperpolarization (i.e., an increase in membrane potential) of taste cells and regulate neurotransmitter release from the cells at chemical synapses with afferent nerve fibers. The primary gustatory sensory fibers, which receive the chemical signals from the sensory cells, enter the base of each taste bud. Inter-cellular connections between taste cells in the same bud may also modulate the signals transmitted to the afferent nerve fibers. Molecules that elicit specific taste sensations are often referred to as "tastants." Although much is known about the psychophysics and physiology of taste cell function, very little is known about the molecules and pathways that mediate its sensory signaling response.

In general, each taste modality is associated with particular types of receptor proteins expressed in some of the cells that form each taste bud. Genes encoding taste receptor proteins for sweet, bitter, umami and salty taste substances have been cloned from a variety of species, including humans. The nature of the coupling of stimulus-receptor interaction to a cellular response in the receptor cells has also been defined for some receptors. Some of these receptors have been used to develop bioassays for use in identifying potential taste enhancers, blockers and modifiers. Although these "chip" based systems have the potential for high throughput screening of large numbers of compounds, they do not incorporate the normal cellular components of the taste signaling pathways that are required for normal receptor-response coupling. Consequently, these assays are best at providing initial information about binding of potential stimuli with a particular receptor. They do not, however, provide information about a subsequent cellular response, if any, to the test substance.

An alternative approach is to express cloned taste receptors in heterologous cells, typically a mammalian cell line such as human embryonic kidney cells (HEK293), and to measure changes in intracellular calcium induced by taste stimuli. This approach requires coupling between stimulus-receptor interaction and a cellular pathway leading to an increase in calcium, and it permits measurements in many cells at once. The normal cellular organization of the taste receptor unit, the taste bud, however, is lost along with any processing of taste information occurring between cells within the taste bud. This limitation is particularly important in light of recent results suggesting that sweet and bitter receptors are localized in taste cells that do not directly communicate with afferent nerve fibers, but rather communicate with adjacent taste bud cells that are innervated.

SUMMARY OF THE INVENTION

Over the years substantial efforts have been directed to the development of various agents that interact with taste receptors to mimic or block natural taste stimulants. Examples of agents that have been developed to mimic sweet tastes are saccharin, monellin, and the thaumatins. Many taste-mimicking or taste-blocking agents developed to-date are not suitable as food additives, however, because they are not economical, are high in calories, or are carcinogenic. Development of new agents that mimic or block the basic tastes has been limited by a lack of knowledge of the taste cell biology involved in the transduction of taste modalities. Thus, there is a continuing need for new products and methods involved in or affect taste transduction.

The present invention provides a method for determining the functional cellular response of a taste cell or taste cells contained in a section of taste-bud containing lingual epithelium (i.e., taste sensory cells in taste bud-containing intact epithelial tissue) to one or more stimuli. In the present invention, one contacts tissue such as taste tissue (such as taste bud-containing epithelial tissues or taste papillae), from an animal, with one or more stimuli, and quantitatively determines the magnitude of at least one cellular signaling event initiated by the stimulus/stimuli. Multiple data values may be collected, such as at differing concentrations of stimulus/stimuli and/or at different time points. The term "isolated taste bud-containing intact epithelial tissue" refers to a tissue sample isolated from an animal, where the tissue has been removed such that the tissue, and the cells contained in the tissue, retains its integrity. For example, the isolated intact taste tissue may be an intact taste bud in an intact lingual epithelial tissue sample that includes precursor cells, support cells, and taste receptor cells such that the polarization of the epithelium is retained. Taste cells have an apical surface and a basal surface. In certain embodiments of the present invention, the stimuli contact the apical surface of the taste cell or cells, but does not contact basal surface of the cell or cells.

The invention provides methods of testing different taste stimuli, e.g., activators, inhibitors, stimulators, enhancers, agonists, and antagonists of taste cells and tissues. As used herein, the term "taste cells" include neuroepithelial cells that are organized into groups to form taste buds of the tongue in structures known as papillae, e.g., foliate, fungiform, and circumvallate papillae (see, e.g., Roper et al. (1989)). Taste cells also include cells of the palate and other tissues that may contain taste cells, such as the esophagus, the stomach, the gastrointestinal tract or other internal organs such as the liver or pancreas. The taste cells may be taken from a biological sample. Such samples include, but are not limited to, tissue isolated from humans, mice, rats, and pigs. In addition to fresh tissue, biological samples may include sections of tissues such as frozen sections taken for histological purposes. A biological sample is typically obtained from a eukaryotic organism, such as an insect, protozoa, bird, fish, reptile, or mammal (e.g., a rat, mouse, cow, dog, pig, rabbit, chimpanzee, or human). Tissues include tongue tissue and isolated taste buds.

A "functional cellular response" in the context of the present invention includes one or more cellular changes in response to any parameter that is indirectly or directly under the influence of the test stimulus, e.g., a functional, physical or chemical effect of the stimulus on the taste cell, cells, or tissue. A functional cellular response includes ligand binding, changes in ion flux, membrane potential, current flow, transcription, signal transduction, receptor-ligand interactions, messenger concentrations (including, but not limited to, cyclic AMP (cAMP), inositol trisphosphate ($IP_3$), or intracellular $Ca^{++}$ or other positive and/or negative ions including, but not limited to, chloride, sodium, or protons), in vitro, in vivo, and ex vivo and also includes other physiologic effects, such as increases or decreases of neurotransmitter or hormone release.

As used herein, "determining a functional cellular response," means assaying for an increase or decrease in a parameter in or on a cell that is indirectly or directly under the influence of the test stimulus, e.g., functional, physical and chemical effects. Such functional effects can be measured by any means known to those skilled in the art, e.g., changes in optical or spectroscopic characteristics (e.g., fluorescence, absorbance, refractive index), hydrodynamic (e.g., shape), chromatographic, or solubility properties, patch clamping, voltage-sensitive dyes, whole cell currents, radioisotope efflux (or influx), inducible markers; tissue culture cell expression; transcriptional activation; ligand binding assays; voltage, membrane potential and conductance changes; ion flux assays; changes in intracellular second messengers such as cAMP and inositol triphosphate (IP3); changes in intracellular calcium levels; neurotransmitter release, and the like. "Inhibitors," "activators," and "modulators" are used to refer to inhibitory, activating, or modulating molecules identified using in vitro and in vivo assays for taste transduction, e.g., ligands, agonists, antagonists, and their homologs and mimetics. Inhibitors are compounds that, e.g., bind to a cell or cell component (e.g., receptor), partially or totally block stimulation, decrease, prevent, delay activation, inactivate, desensitize, or down regulate taste transduction, e.g., antagonists. Activators are compounds that, e.g., bind to a cell or cell component (e.g., receptor), stimulate, increase, activate, facilitate, enhance activation, sensitize or up regulate taste transduction, e.g., agonists. Modulators include compounds that alter the interaction of a polypeptide with receptors or extracellular proteins that bind activators or inhibitor, such as kinases. Modulators include genetically modified, naturally occurring and synthetic ligands, antagonists, agonists, small chemical molecules and the like. Such assays for inhibitors and activators include, e.g., applying putative modulator compounds, in the presence or absence of tastants, and then determining the functional effects on taste transduction. Samples or assays comprising a cell in intact taste tissue but that are treated with a potential activator, inhibitor, or modulator are compared to control samples without the inhibitor, activator, or modulator to examine the extent of modulation. Positive control samples (e.g., a tastant without added modulators) are assigned a relative activity value of 100%. Samples treated with an inhibitor, activator, or modulator are compared to control samples without the inhibitor, activator, or modulator to examine the extent of inhibition, activation or modulation. Control samples (untreated with an inhibitor, activator, or modulator) are assigned a relative activity value of 100%. Inhibition is achieved when the activity value relative to the control is about 80%, optionally 50%, or 25, or even 0%. Activation is achieved when the activity value relative to the control is 110%, optionally 150%, optionally 200-500%, or 1000-3000%, or higher.

The present invention provides a method for simulating a taste, comprising ascertaining the extent to which a cell in intact taste tissue interacts with a tastant. Interaction of a tastant with a cell in intact taste tissue can be determined using any of the assays described herein. The tastant can be combined with other tastants to form a mixture. If desired, one or more of the plurality of the compounds can be combined covalently.

The present invention also provides a method wherein one or more control tastants are tested against one or more test tastants, to ascertain the extent to which a sensory cell or group of sensory cells in taste bud-containing lingual epithelial tissue interacts with each control tastants, thereby generating a stimulation profile for each control tastants. These stimulation profiles may then be stored in a relational database on a data storage medium. The method may further comprise providing a desired stimulation profile for a taste; comparing the desired stimulation profile to the relational database; and ascertaining one or more combinations of control tastants that most closely match the desired stimulation profile. The method may further comprise combining control tastants in one or more of the ascertained combinations to simulate the taste.

The invention also provides methods of screening for modulators, e.g., activators, inhibitors, stimulators, enhancers, agonists, and antagonists, of tastants. Such modulators of taste transduction are useful for pharmacological, chemical, and genetic modulation of taste signaling pathways. These methods of screening can be used to identify high affinity agonists and antagonists of taste cell activity. These modulatory compounds can then be used in the food and pharmaceutical industries to customize taste, e.g., to modulate the tastes of foods, beverages, or drugs.

An "ingestible substance" is a food, beverage, or other comestible, or orally administered products or compositions. A "flavor" herein refers to the perception of taste and/or smell in a subject, which include sweet, sour, salty, bitter, umami, and others. The subject may be a human or an animal. A "flavoring agent" herein refers to a compound or a biologically acceptable salt thereof that induces a flavor or taste in an animal or a human. A "flavor modifier" herein refers to a compound or biologically acceptable salt thereof that modulates, including enhancing or potentiating, and inducing, the tastes and/or smell of a natural or synthetic flavoring agent in an animal or a human. A "flavor enhancer" herein refers to a compound or biologically acceptable salt thereof that enhances the tastes or smell of a natural or synthetic flavoring agent.

"Savory flavor" herein refers to the savory "umami" taste typically induced by MSG (mono sodium glutamate) in an animal or a human. "Savory flavoring agent" or "savory compound" herein refers to a compound or biologically acceptable salt thereof that elicits a detectable savory flavor in a subject, e.g., MSG (mono sodium glutamate). A "savory flavor modifier" herein refers to a compound or biologically acceptable salt thereof that modulates, including enhancing or potentiating, inducing, and blocking, the savory taste of a natural or synthetic savory flavoring agents, e.g., monosodium glutamate (MSG) in an animal or a human. A "savory flavor enhancer" herein refers to a compound or biologically acceptable salt thereof that enhances or potentiates the savory taste of a natural or synthetic savory flavoring agents, e.g., monosodium glutamate (MSG) in an animal or a human.

A "savory flavoring agent amount" herein refers to an amount of a compound that is sufficient to induce savory taste in a comestible or medicinal product or composition, or a precursor thereof. A fairly broad range of a savory flavoring agent amount can be from about 0.001 parts per million (ppm) to 100 ppm, or a narrow range from about 0.1 ppm to about 10 ppm. Alternative ranges of savory flavoring agent amounts can be from about 0.01 ppm to about 30 ppm, from about 0.05 ppm to about 15 ppm, from about 0.1 ppm to about 5 ppm, or from about 0.1 ppm to about 3 ppm.

A "savory flavor modulating amount" herein refers to an amount of a compound that is sufficient to alter (either increase or decrease) savory taste in a comestible or medicinal product or composition, or a precursor thereof, sufficiently to be perceived by a human subject. A fairly broad range of a savory flavor modulating amount can be from about 0.001 ppm to 100 ppm, or a narrow range from about 0.1 ppm to about 10 ppm. Alternative ranges of savory flavor modulating amounts can be from about 0.01 ppm to about 30 ppm, from about 0.05 ppm to about 15 ppm, from about 0.1 ppm to about 5 ppm, or from about 0.1 ppm to about 3 ppm.

A "savory flavor enhancing amount" herein refers to an amount of a compound that is sufficient to enhance the taste of a natural or synthetic flavoring agents, e.g., monosodium glutamate (MSG) in a comestible or medicinal product or composition. A fairly broad range of a savory flavor enhancing amount can be from about 0.001 ppm to 100 ppm, or a narrow range from about 0.1 ppm to about 10 ppm. Alternative ranges of savory flavor enhancing amounts can be from about 0.01 ppm to about 30 ppm, from about 0.05 ppm to about 15 ppm, from about 0.1 ppm to about 5 ppm, or from about 0.1 ppm to about 3 ppm.

Similar definitions are applicable to the other taste modalities of sweet, sour, salty, and bitter.

The terms "isolated," "purified" or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography.

A "label" or a "detectable moiety" is a material having a detectable physical or chemical property, e.g., spectroscopic, photochemical, biochemical, immunochemical, or chemical means. For example, useful labels include fluorescent dyes (e.g., fluorescein isothiocyanate, Texas red, rhodamine, and the like), radiolabels (e.g., $^3$H, $^{125}$I, $^{35}$S, $^{14}$C, or $^{32}$P) electron-dense reagents, enzymes (e.g., horse radish peroxidase, alkaline phosphatase and others), biotin, digoxigenin, or haptens and proteins that can be made detectable, e.g., by incorporating a radiolabel into the peptide.

As used herein, the terms "a" and "an" can mean either single or plural.

BRIEF DESCRIPTION OF THE FIGURES

This patent or application file contains at least one drawing executed in color. Copies of this patent or patent application publication with color drawing(s) will be provided by the Office upon request and payment of the necessary fee.

FIGS. 4A-4D. Multi-Photon Fluorescence Intensity (MP) and Lifetime (MP-FLIM) images of a 1-micron diameter sphere taken with a 63× objective with hardware zoom of 20 (~45 nm per pixel). The data were taken with the CLSM scanning in the x/y plane and in the x/z plane; the relatively low resolution in the x/z direction is consistent with literature values and optical theory. FIG. 4A is MP-FLIM x/y; FIG. 4B is MP-FLIM x/z; FIG. 4C is MP x/y; and FIG. 4D is MP x/z.

FIGS. 5A and 5B. x/y plane Point Spread Function (PSF) rendered from the MP x/y image in FIG. 4 above. To match the conditions under which taste cell data are collected (in this case, 63× obj w. zoom 2), the original image had to be down-sampled by 10×. The resulting PSF is on a 25×25 pixel grid (reduced from the original 256×256 grid). FIG. 5A shows PSF at 63×, zoom 2. FIG. 5B shows PSF at 63×, zoom 20.

FIG. 6A shows a raw taste cell MP image. FIG. 6B shows 100 liters of L-R algorithm with 3× finer-grid PSF. FIG. 6C shows DeNoising of L-R image using $4^{th}$-order PDE method.

FIG. 7A shows unregistered #100, FIG. 7B shows reference #1, and FIG. 7C shows Registered #100.

FIG. 11A shows baseline corrected average intensity per cell, 20 mmol/L citric acid stimulus 1; FIG. 11B shows baseline corrected average intensity per cell, 20 mmol/L citric acid stimulus 2, and FIG. 11C shows baseline corrected average intensity per cell, 20 mmol/L citric acid stimulus 3.

DETAILED DESCRIPTION OF THE INVENTION

Figure 1:
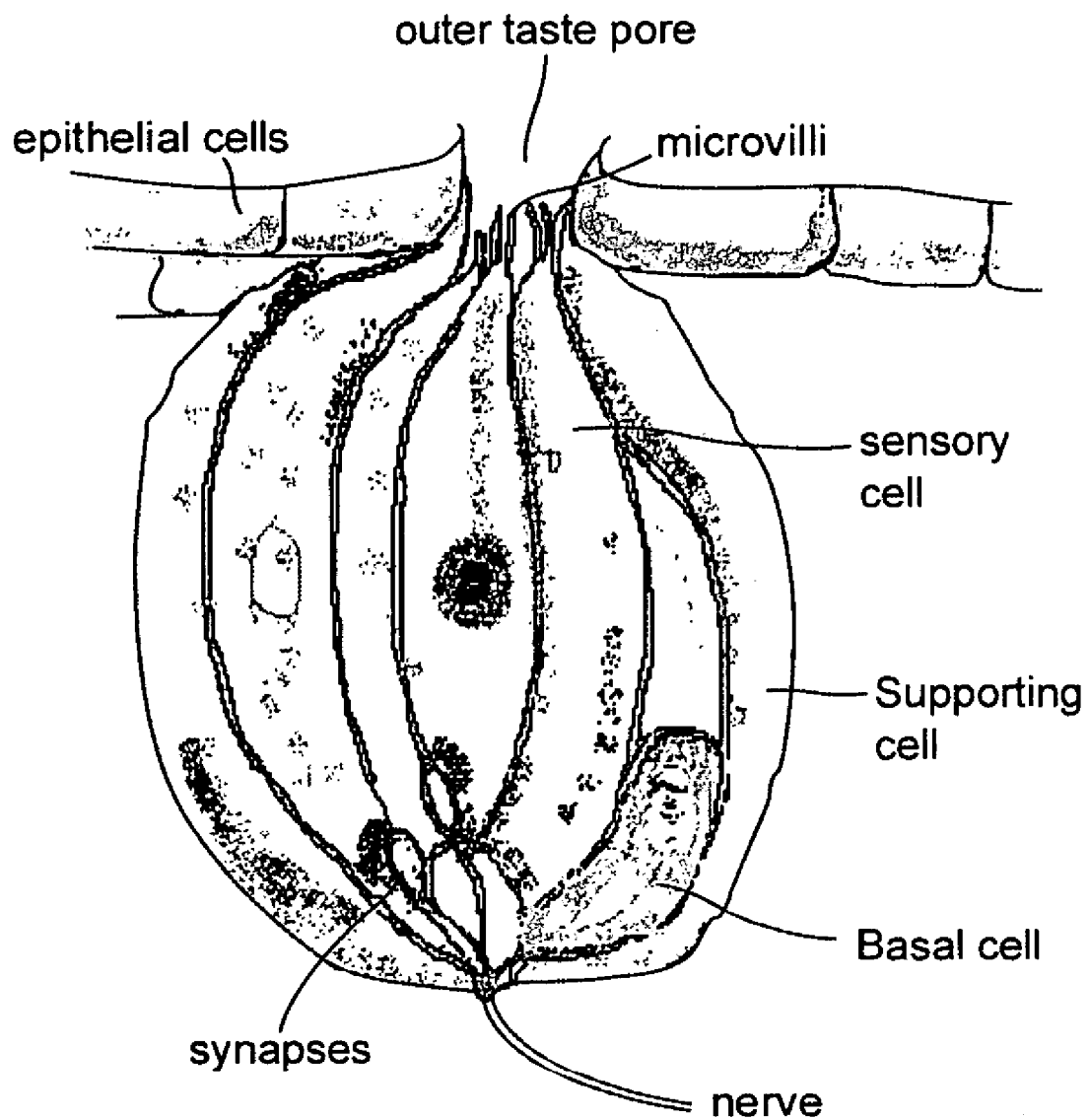
FIG. 1 is a schematic drawing of a taste bud. This figure was found on the World Wide Web at cf.ac.uk/biosi/staff/jacob/teaching/sensory/papillae.gif.

Functional Organization of the Vertebrate Taste Bud

General Anatomic Features of the Peripheral Taste System

Taste buds contain 50-100 polarized neuroepithelial cells of several distinct morphological and immunohistochemical types, at least some of which function as the receptor cells mediating taste signal transduction. (Witt and Reutter, 1996; Finger and Simon, 2000). Three morphological classes of taste bud cells are readily distinguished in all vertebrates: dark (type I), light (type II) and basal or progenitor cells. However, intermediate cells with an appearance intermediate between dark and light cells (rodents), type III cells (initially in rabbits, but much less obvious in rodents), and Merkel-like basal cells (urodele amphibians) have also been described in some species. Additionally, classification of the cell types comprising the taste bud is further complicated by the presence of cells at different stages of development resulting from the replacement of taste cells throughout life.

Type III cells were first described in rabbits (Murray, 1973). They resemble type II cells in general morphological features, but have dense-cored vesicles in the cytoplasm around the nucleus (Takeda and Hoshino, 1975) and show serotonin-like immunoreactivity (LIR) (Uchida, 1985; Fujimoto et al., 1987; Kim and Roper, 1995). Initially, type III cells were not described in rats and mice, although cells with numerous large, dense-cored vesicles were described (Takeda and Hoshino, 1975). Also, a small subset of rodent taste cells have serotonin-LIR, which is markedly enhanced by pre-treatment with the immediate serotonin precursor, 5-HTP (Kim and Roper, 1995; Bourne and Kinnamon, 1999). In rabbit, presynaptic taste cells, i.e., those making afferent synapse onto nerve fibers, are type III cells (Murray, 1973; Royer and Kinnamon, 1991). Recent work, performed largely in Kinnamon's lab, has begun classifying the intermediate cells of rodents, some of which are serotonergic, as type III cells. All three elongated taste cell types in the mouse, type I, intermediate, and type II cells, have been described to have synaptic contacts with nerve fibers (Kinnamon et al., 1985; Kinnamon et al., 1988; Royer and Kinnamon, 1994). These afferent synapses are of two structural types; macular and finger-like (Kinnamon et al., 1985, Kinnamon et al., 1988, Kinnamon et al., 1993; Royer and Kinnamon, 1994). While this is consistent with earlier work in fish showing that both light and dark cells made synaptic contacts with nerve fibers or basal cells (Reutter, 1971). In rats, only intermediate or serotonergic (now called type III) cells make classical synaptic contacts with nerve fibers.

Immunohistochemistry of Taste Cells

The presence of serotonin-LIR in cells in rat taste buds that also have some of the morphological features of intermediate cells has led to their tentative classification as type III cells. In circumvallate taste buds, only taste cells with synapses (type III) show immunoreactivity for SNAP-25, a presynaptic membrane protein (Yang et al., 2000). SNAP-25 is also present in most intragemmal and perigemmal nerve fibers. This could mean that these fibers are "presynaptic", i.e., efferent as well as afferent. For example, reciprocal, or two-way, synapses have been described in taste cells found in some amphibians. The presence of SNAP-25 in taste bud nerve fibers could result from transport from the other end of nerve cells, which are presynaptic to higher order cells in the brain stem. In contrast, synaptobrevin, a vesicle-associated membrane protein (VAMP) believed to function with SNAP-25 to coordinate synaptic vesicle docking and release of neurotransmitter, appears to be present in both type III cells (also showing NCAM-, SNAP-25-, and serotonin-LIR) and a subset of type II cells (which also display taste signal transduction components such as PLCβ2 and IP3R3 (Yang et al. 2004). This suggests that type I cells have "unconventional" synapses that have not been recognized by TEM ultrastructure studies (see Clapp, et. al, 2004).

Taste transduction components associated with G-protein-coupled receptors, IP3R3, PLCβ2, TRPM5 and Gγ13, are expressed in a large subset of type II and a small subset of type III vallate taste cells in rat (Clapp et al., 2004). NCAM is present in many intermediate cells (type III cells) (Nelson and Finger, 1993). 5-HT-LIR and PGP9.5-LIR are present in mutually exclusive subsets of type III cells, but PGP9.5 also in some type II cells (Yee et al., 2003). PLC signaling components are in a vast majority of type II cells and small subset of type III cells. Brain derived neurotrophic factor (BDNF) appears to be in all type III cells, but only a small subset of type II cells (Yee et al. 2003). Only type III cells in rat have conventional synapses with nerve fibers.

Functional Responses of the Taste System

Although a variety of functional cell markers have been used in rodent taste buds, the results are somewhat confusing with regard to classical morphological cell types. A variety of subsets of presumably functionally distinct taste cells appears to exist. Using antigen H (blood type antigen) to mark type I cells, antigen A for type II cells and NCAM for type III cells, Medler, et al. (2003) identified the types of voltage-gated currents in CV and foliate taste cells of mouse. Classified in this way, all type I cells and many type II cells displayed small voltage-gated sodium and potassium currents and no calcium currents. A subset of type II cells and all type III cells had large Na and K currents as well as voltage-gated Ca currents. Unexpectedly, the subset of type II cells that were gustducin positive lacked Ca currents. These results are consistent with the idea that type III cells have synapses with nerve fibers, but that type II cells with G-protein-coupled receptors do not have conventional chemical synapses.

Also, Lyall et al., 2005 and Lyall et al., 2004 have implicated a novel vanilloid receptor variant in mediating the amiloride-insensitive component of the salt taste response in mammals. However, these data do not completely rule out a role for epithelial sodium channels (EN-aCs) in salt taste responses.

There is growing evidence from physiological studies (Finger et al., 2005; Baryshnikov et al. 2003) that ATP plays a role as a neurotransmitter in the taste system. Knockout mice for P2X and/or P3X ionotropic receptors have greatly compromised taste responses. Baryshnikov et al., in contrast, show that P2Y (metabotropic) ATP receptors are present on mouse taste cells and are activated by ATP via a PLC, IP3 cascade that releases internal Ca, followed by an influx of Ca. P2X receptors are present on nerve fibers and could mediate responses to ATP released from taste cells. P2Y receptors on taste cells, however, could mediate neuromodulatory responses to ATP from other taste cells or to ATP released from efferent nerve endings.

There is also the recent work with neuropeptides Y (NPY) cholecystokinin and other neuropeptides (Herness et al., 2005) These substances are released by taste cells and appear to have both autocrine effects on the releasing cell and endocrine effects on neighboring cells. They presumably act as neuromodulators in setting the responsiveness or sensitivities of taste receptor cells. The overlap of NPY with cholecystokinin or vasoactive intestinal peptide was 100%. Given the opposite effects of NPY and the other peptides on cellular responsiveness, this suggests a push-pull system in a given cell.

The present invention provides a method for determining the functional cellular response of taste bud-containing lingual epithelial tissue to one or more stimuli. The tissue to be tested includes live, intact taste cells. The tissue may be obtained from an animal in the form of a biopsy, or may be obtained immediately after sacrifice of an animal (e.g., pig). The tissue is prepared for further study. In one embodiment, the harvested tissue is prepared into slices. In another embodiment, individual papillae are isolated. In another embodiment, individual taste papillae with functional taste buds are isolated. The isolated tissue is then placed either in or on a solid substrate, such as a microscope cover slip. The solid substrate may be coated with a tissue-adhering coating. The tissue may then be placed in a tissue chamber that allows for perfusion of oxygenated cell media and stimuli.

The tissue to be tested may be contacted with a label or a detectable moiety. For example, the tissue may be contacted with a fluorescent dye. In certain embodiments, a dye may be loaded into a tissue or cell or group of cells.

The tissue to be tested is contacted with one or more test taste stimuli, such as activators, inhibitors, stimulators, enhancers, agonists, and antagonists of taste cells and tissues such that exposure of the taste cells to stimuli is isolated to the apical ends of the taste cells through the taste pore. The contacting may be achieved by point delivery by proximate delivery of stimulus via micropipette to the taste pore region, or by bulk delivery via perfusion of a known stimulant concentration (i.e., bathing the tissue in stimulant). The stimulus may be in contact with the tissue briefly (e.g., for a few seconds), or for an extended period of time (e.g., for a few minutes). Further, the stimulus may be in contact with the tissue for a period of time, discontinued for a period of time, and then reapplied. This cycling can be repeated numerous times. Alternatively, the stimulus may be applied at one concentration, and then at a later time period, the stimulus may be applied at another concentration, either higher or lower.

One then detects and/or quantitatively determines the magnitude of at least one cellular signaling event initiated by the stimulus/stimuli. A wide variety of techniques and technologies may be used. Examples include wide field fluorescence imaging using native fluorescence or fluorophores with specific binding properties, confocal laser scanning microscopy (e.g., multiphoton confocal laser scanning microscopy). Multiple data values may be collected, such as at differing concentrations of stimulus/stimuli and/or at different time points.

In the method of the present invention, one quantitatively determines the cellular signaling in response to the one or more stimuli. For example, one could determine the cellular signaling response in the absence of a stimulus, determine the response in the presence of the stimulus, and even then determine the response after the stimulus has been removed. In other words, different temporal measurements can be determined and different concentration measurements can be determined.

Live, Intact Taste Cells/Buds/Tissue

The approach of the present invention permits direct documentation of lateral interactions among cells within taste buds. Several approaches are presented that allow for response measurement of taste tissue system. The taste bud tissue may be extracted from live test subjects from the species under study or from sacrificed animals. Taste cells may be obtained from appropriately sectioned taste papillae and used as thick sections (200 micrometers thick) that would contain a majority of the taste cell and bud structure in the section. The slice preparation provides experimental access to nearly intact taste buds, which retain most of the morphological and functional organization of in situ taste buds.

A taste bud slice preparation also provides the ability to determine if taste responses are modified by lateral and/or sequential processes in cells within the taste buds. For example, dyes sensitive to membrane potential can be used to measure concurrent electrical responses in taste cells. Membrane dyes can also be used to measure synaptic vesicle recycling to determine which cells release neurotransmitter in response to a taste stimulus. Dyes such as Lucifer yellow can be used to assess the effects of electrical coupling between taste cells on signal processing.

For example, in the case of porcine tissue, an intact tongue is procured from a local slaughterhouse and immediately placed in chilled storage (0° C.) for transport to the laboratory. The tongue is then examined and sections of tissue are removed containing fungiform papillae from the lateral portion of the tongue. The tissue sections in this case contain not only epithelial tissue, but taste cells and the connective tissue underneath the papillae. The section, or sections, removed in this manner are placed in an appropriate oxygenated storage solution, as described in the references such as Danilova et al., 1999. In another embodiment, a biopsy is removed from a live animal (e.g., pig) and immediately prepared for examination.

In one embodiment, the tissue section is prepared (e.g., using a vibrating microtome) into a slice section of thickness between 100 and 200 micrometers. This is accomplished using chilled tissue and storage solution such that the sections are cut with minimal cutting artifacts. The individual tissue sections are then placed onto a microscope cover slip coated with a tissue-adhering coating or protein (collagen is typically used). This cover slip is then attached, via suitable removable adhesive or highly viscous, non-reacting grease, to a tissue chamber that allows for perfusion of oxygenated cell media and stimuli. This presentation is then ready to be loaded with appropriate cell signaling dye and imaged for response to stimulus as a slice section. Alternately, the slice section may be prepared, in a manner similar to that above, after the papillae tissue is loaded with an appropriate signaling dye.

An alternate approach is to utilize intact preparations of taste tissue excised from the tongue as papilla tissue, with epithelial cells and an intact taste pore located on the top of the tissue. For example, a subject animal (e.g., pig or human) is anaesthetized and biopsied along the lateral portion of the tongue, resulting in removal of a block of tissue one to two millimeters on a side. This tissue is then placed directly in chilled storage solution and prepared, under a dissecting microscope, into a tissue sample containing a single fungiform papilla. This is then transferred to a cover slip such that the apical face of the taste bud is pointing up from the cover slip, exposing the taste pore and surrounding epithelial tissue, and the basolateral portion of the papilla is attached to the coverslip over a small hole, allowing for perfusion of the tissue from the basolateral side. The tissue may be adhered to the coverslip via a coating of collagen or the application of tissue cement to the edges of the papilla in contact with the coverslip. This sample is thus prepared for subsequent loading of appropriate signaling dye. Examples of general taste tissue preparation and loading protocols and results are given in the following references: Lindemann, 1996; and Caicedo et al., 2000.

Taste tissue (taste buds or taste papillae) can be isolated from a wide variety of animals. For instance, rodents are subjects of studies involving stimulation of taste sensory systems in the work presented in Caicedo et al., 2000. In addition, feline specimens have been used for taste response studies, according to the following references: Boudreau et al., 1973; Boudreau et al. 1977; Boudreau et al. 1971; Krimm et al. 1998; and Boudreau et al. 1985. Additionally, canines are subjects of studies involving stimulus of taste sensory systems in the work presented in the following references: Kumazawa et al., 1990; Kumazawa et al., 1991; Kumazawa et al., 1990; Nakamura et al. 1990; and Nakamura et al. 1991.

The isolation of taste sensory systems (taste buds or taste papillae) from taste tissue is not limited to mammalian subjects. For instance, species of fish have been the subject of taste system study, according to the following representative references: Caprio, J. 1975; Brand et al., 1991; Zviman et al. 1996; Hayashi et al., 1996; Finger et al., 1996; and Ashworth 2004.

Imaging System Consisting of Fluorescence Imaging of Cellular Signaling Events

The imaging of cellular signaling events is performed using a variety of techniques and technologies. The prevailing tool in this area of endeavor is optical microscopy of fluorescent structures and features in cells, which encompasses a broad spectrum of specific equipment and approaches. First, wide field fluorescence imaging using both native fluorescence and addition of fluorophores with specific binding properties to cell species is a widely used tool. In addition, confocal laser scanning microscopy (CLSM) of fluorescently labeled cells with ultraviolet or visible light excitation is a tool gaining increased use in cell studies. Alternatively, confocal laser scanning microscopy of fluorescently labeled cells with multiphoton excitation using a near-infrared laser is a methodology that allows for deeper tissue sampling and reduced tissue damage due to the optical effects exploited in multiphoton excitation of fluorescent molecules.

Fluorescence is the result of a three-stage process that occurs in certain molecules (generally polyaromatic hydrocarbons or heterocycles) called fluorophores or fluorescent dyes. A fluorescent probe is a fluorophore designed to localize within a specific region of a biological specimen or to respond to a specific stimulus.

In stage one, a photon of energy $h\nu_{EX}$ is supplied by an external source such as an incandescent lamp or a laser and absorbed by the fluorophore, creating an excited electronic singlet state ($S_1'$). This process distinguishes fluorescence from chemiluminescence, in which the excited state is populated by a chemical reaction.

In stage two, the excited state exists for a finite time (typically 1-10 nanoseconds). During this time, the fluorophore undergoes conformational changes and is also subject to a multitude of possible interactions with its molecular environment. These processes have two important consequences. First, the energy of $S_1'$ is partially dissipated, yielding a relaxed singlet excited state ($S_1$) from which fluorescence emission originates. Second, not all the molecules initially excited by absorption (stage one) return to the ground state ($S_0$) by fluorescence emission. Other processes such as collisional quenching, fluorescence resonance energy transfer (FRET) and intersystem crossing (see below) may also depopulate $S_1$. The fluorescence quantum yield, which is the ratio of the number of fluorescence photons emitted (Stage 3) to the number of photons absorbed (Stage 1), is a measure of the relative extent to which these processes occur.

During stage three of the fluorescence excitation/emission process, a photon of energy $h\nu_{EM}$ is emitted, returning the fluorophore to its ground state $S_0$. Due to energy dissipation during the excited-state lifetime, the energy of this photon is lower, and therefore of longer wavelength, than the excitation photon $h\nu_{EX}$. The difference in energy or wavelength represented by ($h\nu_{EX}-h\nu_{EM}$) is called the Stokes shift. The Stokes shift is fundamental to the sensitivity of fluorescence techniques because it allows emission photons to be detected against a low background, isolated from excitation photons. In contrast, absorption spectrophotometry requires measurement of transmitted light relative to high incident light levels at the same wavelength.

The entire fluorescence process is cyclical. Unless the fluorophore is irreversibly destroyed in the excited state (an important phenomenon known as photobleaching, see below), the same fluorophore can be repeatedly excited and detected. The fact that a single fluorophore can generate many thousands of detectable photons is fundamental to the high sensitivity of fluorescence detection techniques. For polyatomic molecules in solution, the discrete electronic transitions represented by $h\nu_{EX}$ and $h\nu_{EM}$ are replaced by rather broad energy spectra called the fluorescence excitation spectrum and fluorescence emission spectrum, respectively. The bandwidths of these spectra are parameters of particular importance for applications in which two or more different fluorophores are simultaneously detected (see below). With few exceptions, the fluorescence excitation spectrum of a single fluorophore species in dilute solution is identical to its absorption spectrum. Under the same conditions, the fluorescence emission spectrum is independent of the excitation wavelength, due to the partial dissipation of excitation energy during the excited-state lifetime. The emission intensity is proportional to the amplitude of the fluorescence excitation spectrum at the excitation wavelength. Additional information regarding optical processes involved in fluorescence can be found in Lakowizc, J. R., 1999.

Fluorescence microscopy is very useful due to the inherent specificity afforded by the application of fluorescent labels to specific cell targets. As an example, Molecular Probes Corporation markets and sells a complete library of standardized fluorescent tags functionalized to allow for specific assays and tagging experiments. For instance, calcium sensitive dyes respond to changes in intracellular calcium ion concentration by changing the excitation or emission properties of the dye. For the calcium ion indicators fura-2 and indo-1 the free and ion-bound forms of fluorescent ion indicators have different emission or excitation spectra. With this type of indicator, the ratio of the optical signals can be used to monitor the association equilibrium and to calculate ion concentrations. Ratiometric measurements eliminate distortions of data caused by photobleaching and variations in probe loading and retention, as well as by instrumental factors such as illumination stability. Lifetime measurements of fluorophores in different environments allow for quantitative measurement of the environment perturbation, regardless of differences in dye distribution and optical scattering, making this an attractive mode of measurement in living tissue.

Wide-field fluorescence microscopy is very widely used to obtain both topographical and dynamic information. It relies on the simultaneous illumination of the whole sample. The source of light is usually a mercury lamp, giving out pure white light. Optical filters are then used in order to select the wavelength of excitation light (the excitation filter). Excitation light is directed to the sample via a dichroic mirror (i.e., a mirror that reflects some wavelengths but is transparent to others) and fluorescent light detected by a camera (usually a CCD camera). Thus both the illumination and detection of light covering the whole visual field of the chosen microscope objective is achieved simultaneously.

Alternatively, laser scanning confocal microscopy (LSCM or CLSM, abbreviated CLSM in this document) may be used to excite and collect fluorescence from a system under study. Measuring fluorescence by CLSM differs from wide-field fluorescence microscopy in a number of ways. First, the light source is one or more laser(s). This has two consequences. First, the excitation light bandwidth is determined by the source, not the excitation filter and thus is much narrower than in wide field fluorescence microscopy (2-3 nm rather than 20-30 nm). Second, in order to illuminate the whole visual field, the laser beam has to be rapidly scanned across the area in a series of lines, much like a TV image is generated. The fluorescence detected at each point is measured in a photomultiplier tube (PMT), and an image is built up. This method of illumination has enormous advantages in that it is possible to illuminate selected regions of the visual field allowing complex photobleaching protocols to be carried out to investigate the rates of lateral travel of fluorophores and for the excitation of different fluorophores in different regions of the same cell. The major difference between fluorescence microscopy and CLSM is the presence of a pinhole in the optical path. This is a device that removes unwanted, out-of-focus fluorescence, giving an optical slice of a 3-dimensional image. In one embodiment of the imaging protocol, excitation light incident on the sample excites the object of interest, and gives high-resolution fluorescent image with a minimum amount of haze or out-of-focus light reaching the detector. In order to obtain such an image, the pinhole is placed in front of the detector photomultiplier tube and blocks the passage of this out-of-focus light into the PMT. This means that the only light to enter the PMT, and thus be detected, comes from near the focal plane of the objective lens of the microscope. As this is taken across the area of the sample, it produces an image that is a slice through the object and surrounding material. This is known as "optical slicing" and allows the observer to see inside the object of interest. This gives clear images, with fine detail observable.

In addition to the above advantages, by altering the focus of the microscope, images can be obtained at different depths. Each image is called a z-section, and can be used to reconstruct an image of the 3-dimensional object. As an analogy, this technique is like cutting an object into slices, and then stacking the slices back on top of each other to reconstruct the shape of the object. This principle can similarly be achieved using multiple z-sections. If images are "stacked" on top of one another in the correct order, a single three-dimensional image of the object can be generated.

In an alternative embodiment, multiphoton CLSM may be used, where multiphoton excitation of the fluorophores of interest is achieved. As stated earlier, the energy of emitted fluorescent light is less than that of the incident light. Also, fluorophores that absorb red light do not emit green fluorescence. This holds true for almost all fluorescent applications. Under appropriate conditions, however, the generation of high energy fluorescence using low energy incident light is achieved by delivering multiple photons of excitation light to the same point in space in a sufficiently short time that the energy effectively is summed and so acts as a higher energy single photon. The arrival of the first photon causes the electron to become excited, but not sufficiently to reach a more stable state. This excess energy is lost quickly, but if a second photon is delivered rapidly enough, the electron acts as if a high-energy single photon has been delivered, resulting in fluorescence emission from the focal point fluorophores.

The timescale of electronic excitation is incredibly short. The second photon must arrive within <0.1 femtoseconds, so photons must be delivered in rapid succession. The power required to deliver such a rapid continuous stream of photons into a particular position in space, however, is enormous, up to about 1-Terawatt/$cm^2$. In order to prevent damage to biological samples, pulsed lasers are typically used. A typical multiphoton excitation laser is the Titanium: Sapphire laser, which delivers pulses of photons of about 100 femtoseconds duration separated by about 12-40 nanoseconds, at wavelengths ranging from ~700 to 1000 nanometers. Thus, although the pulses of light are of extremely high intensity, the average power delivered to the sample is relatively low.

Several advantages exist with regard to employing multiphoton excitation in fluorescence imaging. First, light from the high intensity red to near infrared laser scatters less efficiently than lower intensity blue light, so objects of interest can be imaged in thicker sections of tissue than in conventional CLSM. Thicker tissue slices are likely to be healthier, and the cells being observed are less likely to have been damaged in the preparation of the sample. Second, the lower overall energy of the excitation light means that less phototoxic damage is caused during viewing and less photobleaching is seen, extending the time that cells can be observed. Third, multiphoton CLSM is innately confocal, i.e., no pinhole is required. Excitation of the fluorophore can occur only where the two photons can interact. Given the quadratic nature of the probability of two photons interacting with the fluorophore in the necessary timescale, excitation occurs only in the focal plane of the objective lens. This provides cleaner images. Finally, the high repetition rate pulsed laser used in multiphoton CLSM is uniquely suited to performing rapid fluorescent lifetime measurements. Thus, a cell with an appropriate calcium sensitive dye, like calcium green dextran, is imaged using multiphoton fluorescence lifetime imaging with a properly configured CLSM to yield deep tissue measurement of intracellular calcium release in a receptor cell, such as a taste receptor cell.

Additional information regarding biological applications of fluorescence microscopy in cell signaling studies may be found in the following references: Gratton et al. 2003; Koester et al., 1999; Konig, K. et al. 1997; Liu et al., 2003.

Quantitative Stimulus Delivery System Applied to Live Tissue

The ability to provide known concentrations of taste stimuli to the preparation under precise temporal and spatial control is critical to quantitative determination of cellular signaling in response to stimulus. The delivery of stimuli may be by any one or several methods. In one embodiment of the present invention, for example, the delivery of stimuli is achieved by point delivery by proximate delivery of stimulus via micropipette to the taste pore region. In another exemplary embodiment, the delivery of stimuli is achieved by bulk delivery via perfusion of known stimulant concentration, effectively bathing the tissue in stimulant.

In one embodiment of a proximate delivery approach, slices of taste papillae containing taste buds are mounted on glass cover slips coated with adhesive protein. The cover slips form the bottom of the recording/perfusion chamber, which is attached to the stage of the microscope. A continuous background flow of oxygenated, physiological saline (e.g., Tyrode solution) is supplied to the chamber from a temperature-controlled reservoir via an independently heated perfusion line. The direction of flow across the slice is oriented from the base to the apical region of the taste bud. Taste stimuli or mixtures of stimuli are applied from an independent, 8-line, temperature-controlled perfusion pencil. Each of seven lines are attached to pressurized solution reservoirs via miniature (normally-closed) solenoid valves. The $8^{th}$ line is attached via a normally-open solenoid valve to a regulated vacuum line and vacuum trap. The solenoids are under computer control so that a stimulus valve opens while the vacuum line is simultaneously closed for a predetermined time. This device is positioned with the delivery tip close to and slightly distal to the apical end of the taste bud. This allows small puffs of up to seven different stimuli to be applied just to the apical, receptive ends of the taste cells. By adjusting the pressure in the stimulus reservoirs, the position of the stimulus delivery tube, and the rate of background perfusion, stimuli can be confined to just the apical surfaces of the taste bud cells. It is desirable to prevent activation of cellular pathways in the basolateral membranes of the taste bud cells that normally do not interact with taste stimuli on the surface of the tongue, which could lead to erroneous conclusions about taste response properties. The vacuum line in the stimulus delivery manifold is typically closed slightly after activation of the chosen stimulus valve and acts to prevent mixing of stimuli by evacuating solution leaking from closed lines and for priming the selected delivery tube. Solutions are continuously removed from the chamber by a vacuum line set to provide a constant fluid level and to pull solution without "jitter" or "slurping" at the solution surface.

In an alternative embodiment, pieces of tongue epithelium containing taste buds are removed from the underlying tissue using gentle enzymatic treatment or via surgical removal. The epithelium is mounted in a trans-epithelial chamber that allows independent perfusion of the basolateral (serosal) and apical (mucosal) surfaces. This permits the normal polarity of the epithelium and the taste buds in it to be maintained. The basolateral chamber is perfused with oxygenated Tyrode solution that has been pre-heated to minimize out-gassing and formation of bubbles. Manipulations of basolateral ion channels and transports are manipulated by application of Tyrode solution containing pharmacological agents by switching to other perfusate reservoirs through a bank of valves. The apical chamber is used either in an open configuration with a dipping objective or closed, with a cover glass attached to the top of the chamber. In either case, stimuli is applied from temperature-controlled reservoirs attached to the apical chamber via computer-controlled solenoid valves attached to a manifold attached to the chamber with a short length of tubing. This system is either gravity fed via constant flow syringes or through pressurized reservoirs. In either case, up to 24 independent stimuli can be applied to the apical chamber and then rinsed out under computer control with the present system. In an alternative stimulus delivery arrangement, the stimulus is delivered via a sample injection loop placed inline with the apical perfusion line. The volume of the injection loop is controlled via loop length, and under static flow rate conditions, the stimulus may be reproducibly introduced into the sample chamber at a known time and using a known concentration.

Collection of Stimulus/Response Data Structure from Imaging/Stimulus System

A stimulus/response data structure may be collected from a live cell preparation in the following general manner. A cell and/or tissue sample is obtained and mounted in a suitable oxygenated bath to allow for live cell imaging. The cell/tissue is exposed to signaling-sensitive fluorescent dye such that the intracellular matrix (or membrane, in the case of membrane potential-sensitive dyes, and recycling synaptic vesicles, in the case of synaptic activity markers) is loaded with dye. The cell and/or tissue sample is transferred to the imaging platform that contains the stimulus system and a perfusion chamber, and supporting apparatus, to allow for constant perfusion of the sample during the experimental data collection. Image data is collected from the cell and/or tissue sample, using appropriate image modality and acquisition parameters to provide a baseline or standard resting response image data matrix prior to quantitative stimulus.

Stimulus or series of stimuli are applied in the form of one or more solutions of known concentrations of stimulus prepared in surrogate or synthetic saliva matrices. The application of stimulus is proximate to the taste pore and is administered via a micropipette system having control of stimulus flow and pipette position. Alternatively, the application of stimulus is administered via the perfusion medium, thus bathing the cell and/or tissue sample in a known concentration of stimulus. Before, during, and after the application of known stimulus to the cell and/or tissue sample, image data are collected in such a manner that a number, if not all, of the cells comprising the taste bud are represented in the field of view captured by the imaging system. The image data are collected in such a manner that data corresponding to multiple time points for each phase (before, during, and after stimulus) are collected. Image data collected at each time point may be comprised of two or three spatial dimensions.

By way of example, an intact pig tongue is procured from a local slaughterhouse and immediately placed in chilled storage (4° C.) for transport to the laboratory. The tongue is then examined and sections of tissue are removed containing fungiform papillae from the lateral portion of the tongue. The tissue sections in this case contain not only epithelial tissue, but also taste cells and the connective tissue underneath the papilla. The section, or sections, removed in this manner are placed in an appropriate oxygenated Tyrode storage solution.

The tissue section is prepared, using a vibrating microtome, into a slice section of thickness between 100 and 200 micrometers. This is performed using chilled tissue and storage solution such that the sections are cut with minimal cutting artifacts. The individual tissue sections are then placed onto a microscope cover slip coated with a tissue-adhering coating or protein (collagen is typically used). This cover slip is then attached, via suitable removable adhesive or highly viscous, non-reacting grease, to a tissue chamber that allows for perfusion of oxygenated cell media and stimuli. This presentation is then iontophoretically loaded with a dye, such as 5 mg/mL calcium green dextran (3000 MW), and imaged for response to glutamate stimulus as a slice section. The loading of calcium sensitive dye is verified via standard wide field epifluorescence microscopy. The tissue slice preparations are then transferred to the measurement chamber on the recording microscope, such as a multiphoton confocal laser scanning microscope with epifluorescence optical filters designed to allow for multiphoton excitation of the dye and recording of emission above 530 nm. A continuous background flow of oxygenated, physiological saline (Tyrode solution) is supplied to the chamber from a temperature-controlled reservoir via an independently heated perfusion line. The direction of flow across the slice is oriented from the base to the apical region of the taste bud. Taste stimuli or mixtures of stimuli are applied from an independent, 8-line, temperature-controlled perfusion pencil. Each of seven lines is attached to pressurized solution reservoirs via miniature (normally-closed) solenoid valves. The $8^{th}$ line is attached via a normally open solenoid valve to a regulated vacuum line and vacuum trap. The solenoids are under computer control so that a stimulus valve opens while the vacuum line is simultaneously closed for a predetermined time. This device is positioned with the delivery tip close to and slightly distal to the apical end of the taste bud.

For stimulus one, at time=zero, the perfusion and stimulus chambers allow flow with no stimulus, and one or more image frames are acquired whereby the intensity of the generated fluorescence is acquired on a per pixel basis along one plane through the tissue, capturing several, if not all, of the cells in the tissue in the field of view. These frames are referred to as the baseline frames, prior to stimulus. After 2-5 minutes of perfusion with no stimulus, a low concentration stimulus of glutamate (0.05 mmol/L) in artificial saliva perfusion medium is applied via a single pipette channel proximate to the taste pore for a predefined length of time, such as 120 seconds. An initial response to the stimulus is recorded via the fluorescence imaging system upon activation of the stimulus channel. Subsequently, two or more additional image frames are recorded during the stimulus time period, generating a series of frames collected during stimulus. The stimulus is then discontinued and the perfusion continues with no stimulus present, effectively rinsing stimulus from the region of interest around the taste pore. After the stimulus is removed, and at time intervals corresponding to 60 seconds, additional frames are recorded using the fluorescence imaging system in order to develop three frames of image data corresponding to the resting, or post stimulus, response of the taste system under study after stimulus one.

For stimulus two, the perfusion and stimulus chambers allow flow with no stimulus, and single image frame is acquired whereby the intensity of the generated fluorescence is acquired on a per pixel basis along one plane through the tissue, capturing several, if not all, of the cells in the tissue in the field of view. This frame is referred to as the baseline frame, prior to stimulus for stimulus two and may be different in intensity from the baseline stimulus one frame. After 2-5 minutes of perfusion with no stimulus, a low concentration stimulus of glutamate (0.25 mmol/L) in artificial saliva perfusion medium is applied via a single pipette channel proximate to the taste pore for a predefined length of time, such as 120 seconds. An initial response to the stimulus is recorded via the fluorescence imaging system upon activation of the stimulus channel. Subsequently, two additional image frames are recorded during the stimulus time period, generating a series of frames collected during stimulus. The stimulus is then discontinued and the perfusion continues with no stimulus present, effectively rinsing stimulus from the region of interest around the taste pore. After the stimulus is removed, and at time intervals corresponding to 60 seconds, additional frames are recorded using the fluorescence imaging system in order to develop three frames of image data corresponding to the resting, or post stimulus, response of the taste system under study after stimulus two.

For stimulus three, the perfusion and stimulus chambers allow flow with no stimulus, and single image frame is acquired whereby the intensity of the generated fluorescence is acquired on a per pixel basis along one plane through the tissue, capturing several, if not all, of the cells in the tissue in the field of view. This frame is referred to as the baseline frame, prior to stimulus for stimulus three and may be different in intensity from the baseline stimulus two frame. After 2-5 minutes of perfusion with no stimulus, a low concentration stimulus of glutamate (0.75 mmol/L) in artificial saliva perfusion medium is applied via a single pipette channel proximate to the taste pore for a predefined length of time, in this case 120 seconds. An initial response to the stimulus is recorded via the fluorescence imaging system upon activation of the stimulus channel. Subsequently, two additional image frames are recorded during the stimulus time period, generating a series of frames collected during stimulus. The stimulus is then discontinued and the perfusion continues with no stimulus present, effectively rinsing stimulus from the region of interest around the taste pore. After the stimulus is removed, and at time intervals corresponding to 60 seconds, additional frames are recorded using the fluorescence imaging system in order to develop three frames of image data corresponding to the resting, or post stimulus, response of the taste system under study after stimulus three. The collection of these three time-dependent stimulus/response image data sets results in single image data structure that is then used to generate a quantitative relationship between stimulus and taste tissue response as determined by intensity-based calcium green dextran fluorescence measurements of changes in intracellular calcium.

An alternative embodiment of this experiment is as follows. A subject pig is anaesthetized and biopsied along the lateral portion of the tongue, resulting in removal of a block of tissue five millimeters on a side. This tissue is then placed directly in chilled storage solution and prepared, under a dissecting microscope, into a tissue sample containing a single fungiform papilla. This is then transferred to a collagen-coated cover slip such that the apical face of the taste bud is pointing up from the cover slip, exposing the taste pore and surrounding epithelial tissue. This cover slip is then attached, via suitable removable adhesive or highly viscous, non-reacting grease, to a tissue chamber that allows for perfusion of oxygenated cell media and stimuli. This presentation is then iontophoretically loaded with 5 mg/mL calcium green dextran (3000 MW) and imaged for response to glucose stimulus as a slice section. The loading of calcium sensitive dye is verified via standard wide field epifluorescence microscopy by application of dye to the apical end of the taste bud through the taste pore.

The intact tissue preparations are then transferred to the measurement chamber on the recording microscope, in this case a multiphoton confocal laser scanning microscope with epifluorescence optical filters designed to allow for multiphoton excitation of the dye and recording of time correlated picosecond fluorescence lifetime emissions above 530 nm in such a manner as to allow for fluorescence lifetime images to be generated. This is accomplished via a time correlated single photon counting detector attached to the output port of the confocal laser-scanning microscope (such as a Leica MP-FLIM system).

The epithelium is mounted in a trans-epithelial chamber that allows independent perfusion of the basolateral (serosal) and apical (mucosal) surfaces. This permits the normal polarity of the epithelium and the taste buds in it to be maintained. The basolateral chamber is perfused with oxygenated Tyrode solution that has been pre-heated to minimize out-gassing and formation of bubbles. Manipulations of basolateral ion channels and transports can be manipulated by application of Tyrode solution containing pharmacological agents by switching to other perfusate reservoirs through a bank of valves. Stimuli are applied from temperature-controlled reservoirs attached to the apical chamber via computer-controlled solenoid valves attached to a manifold attached to the chamber with a short length of tubing.

For stimulus one, at time=zero, the perfusion and stimulus chambers allow flow with no stimulus, and single image frame is acquired whereby the intensity of the generated fluorescence is acquired on a per pixel basis along one plane through the tissue, capturing several if not all of the cells in the tissue in the field of view. This frame is referred to as the baseline frame, prior to stimulus. After 5-7 minutes of perfusion with no stimulus, a low concentration stimulus of glutamate (0.05 mmol/L) in artificial saliva perfusion medium is applied via a single pipette channel proximate to the taste pore for a predefined length of time, in this case 240 seconds. An initial response to the stimulus is recorded via the fluorescence imaging system upon activation of the stimulus channel. Subsequently, two additional image frames are recorded during the stimulus time period, generating a series of frames collected during stimulus. The stimulus is then discontinued and the perfusion continues with no stimulus present, effectively rinsing stimulus from the region of interest around the taste pore. After the stimulus is removed, and at time intervals corresponding to 120 seconds, additional frames are recorded using the fluorescence imaging system in order to develop three frames of image data corresponding to the resting, or post stimulus, response of the taste system under study after stimulus one.

For stimulus two, the perfusion and stimulus chambers allow flow with no stimulus, and single image frame is acquired whereby the intensity of the generated fluorescence is acquired on a per pixel basis along one plane through the tissue, capturing several if not all of the cells in the tissue in the field of view. This frame is referred to as the baseline frame, prior to stimulus for stimulus two and may be different in intensity from the baseline stimulus one frame. After 5-7 minutes of perfusion with no stimulus, a low concentration stimulus of glutamate (0.25 mmol/L) in artificial saliva perfusion medium is applied via a single pipette channel proximate to the taste pore for a predefined length of time, such as 240 seconds. An initial response to the stimulus is recorded via the fluorescence imaging system upon activation of the stimulus channel. Subsequently, two additional image frames are recorded during the stimulus time period, generating a series of frames collected during stimulus. The stimulus is then discontinued and the perfusion continues with no stimulus present, effectively rinsing stimulus from the region of interest around the taste pore. After the stimulus is removed, and at time intervals corresponding to 120 seconds, additional frames are recorded using the fluorescence imaging system in order to develop three frames of image data corresponding to the resting, or post stimulus, response of the taste system under study after stimulus two.

For stimulus three, the perfusion and stimulus chambers allow flow with no stimulus, and single image frame is acquired whereby the intensity of the generated fluorescence is acquired on a per pixel basis along one plane through the tissue, capturing several if not all of the cells in the tissue in the field of view. This frame is referred to as the baseline frame, prior to stimulus for stimulus three and may be different in intensity from the baseline stimulus two frame. After 5-7 minutes of perfusion with no stimulus, a low concentration stimulus of glutamate (0.75 mmol/L) in artificial saliva perfusion medium is applied via a single pipette channel proximate to the taste pore for a predefined length of time, in this case 240 seconds. An initial response to the stimulus is recorded via the fluorescence imaging system upon activation of the stimulus channel. Subsequently, two additional image frames are recorded during the stimulus time period, generating a series of frames collected during stimulus. The stimulus is then discontinued and the perfusion continues with no stimulus present, effectively rinsing stimulus from the region of interest around the taste pore. After the stimulus is removed, and at time intervals corresponding to 120 seconds, additional frames are recorded using the fluorescence imaging system in order to develop three frames of image data corresponding to the resting, or post stimulus, response of the taste system under study after stimulus three. The collection of these three time-dependent stimulus/response image data sets results in single image data structure that is then used to generate quantitative relationship between stimulus and taste tissue response as determined by emission lifetime-based calcium green dextran fluorescence measurements of changes in intracellular calcium.

Quantitative Relationship Development Between Image Data and Stimulus

Once the stimulus-dependent image data are collected, a quantitative relationship between the stimulus applied and the response of the cellular system is developed. This may be achieved by the following stepwise general approach. First, the image data is standardized with respect to feature position (x,y axis), feature intensity (z axis), and feature time (t axis). This includes, e.g., defining onset of stimulus application (initial time or Ti) and the disappearance of stimulus response (final time or Tf) for each series of images associated with a particular stimulus application; registering each image within such a series such that spatial information in each image in the series may be correlated to subsequent images (Ti+1 to Tf) within that series (and collection of series for a sequence of stimulus applications); and normalizing the baseline and dynamic ranges for the responses between each image within such a series.

Next, a Region or Regions of Interest (ROIs) are defined within each of the standardized images that contain phenomena related to the magnitude of the applied stimulus. The information within such ROIs is used to extract vector or scalar quantities that represent the independent variables in the comparison step.

Independent variables from the standardized data ROIs are then extracted. For magnitude or concentration measurements, this includes reducing the collection of pixel values for a given image ROI to a scalar quantity. For temporal measurements, this includes reducing time-dependent intensity changes in lifetime or intensity ratio within a series of image ROIs to vector quantities. For spatial measurements, this includes reducing, e.g., diffusion events across ROIs in the (x,y) space to vector quantities. This may include multiple scalar/vector extractions for more than one ROI within each image. After extraction, the independent variables are then grouped into a single vector to represent a particular stimulus application.

Next, the known stimulus applications (dependent variables) are compared against their corresponding independent variable vectors. The comparison may include elements of classification, regression, or qualitative procedures that are used to rank the data according to the applied stimuli. Such procedures define a model which, when applied to an independent variable vector collected on a stimulated sample in the future, yield a classification estimate or predicted stimulus magnitude. In addition, this procedure yields estimates of statistical quantities such as correlation coefficients for the independent vector components and confidence limits for the classification estimate or stimulus magnitude prediction.

By way of example, image data standardization is begun by applying an intensity correction to each image within the set so that each image's response to a pre-defined internal standard condition is the same. For example, an inert fluorescent dye of known concentration is injected into the field of view along with the applied stimulus, and the response of this dye is defined to have a certain magnitude. Alternatively, the image data set is normalized to maximum and minimum values of intensity and this normalization is applied to subsequent images for comparison.

Following this step, the set of images are corrected for random movement of objects within the field of view during data acquisition. The mathematical procedure of correcting arbitrary differences between a set of multidimensional collections of values is called Procrustes Rotation. Such procedures determine a linear transformation (translation, reflection, orthogonal rotation, and scaling) of the points in a matrix Y (or in this case a digital image) to best conform them to the points in another matrix X. Different methods, such as promax, orthomax, or varimax rotations can be applied, which differ mainly in the criterion they use to estimate differences in the alignment fit. Standardizing the images with respect to time includes defining the onset of stimulus application (initial time or Ti) and the disappearance of stimulus response (final time or Tf) for every collected set of images. Ti could be defined as the first image in the series to show any data point response above a pre-defined baseline or un-stimulated condition, and Tf could be defined as the first image after Ti to register no data point responses above the baseline condition (i.e., the imaged field of view has returned to an "un-stimulated" state).

Having corrected the raw image data, the informative ROIs of the images is then isolated. This can be done manually by having a trained operator input image coordinates or interactively draw perimeters around ROIs in a reference image. A more rigorous way is to calculate the magnitude of response for each data point in the set of images between Ti and Tf. Those values with maximum responses below a certain threshold are discarded as "noise" or "background." Further, the remaining data points are grouped into similar types according to the pattern of their response to the applied stimuli as a function of time. For example, certain regions of the field of view might record transitory "spikes" in response along the time axis, while others demonstrate a steady-state increase in response throughout the entire period from $T_i$ to $T_f$. This pattern recognition can also be done manually. Alternatively, quick mathematical routines such as Principal Components Analysis (PCA) or Cosine Correlation Analysis (CCA) can be used to define the different types of informative data points in the image. Likewise, if temporal information is not important for quantification, the average or summed response of each data point could be calculated across the time axis of a given set of images. Groups of interconnected data points with similar response levels are then defined as individual ROIs. Regardless of the procedure used, the ROI definitions need to be done only once, since all of the images in a set (and across sets collected for the same field of view) have been aligned with respect to each other, so that an ROI in any given image is in the exact same place on all other images within a set, and among different image sets.

Depending upon how the ROIs were defined, the information within them may have to be transformed into scalar or vector quantities to make it appropriate for comparison to the magnitude of the applied stimulus. For temporal measurements, this includes reducing time-dependent intensity changes in lifetime or intensity ratio within a series of image ROIs to vector quantities. The most straightforward way to do this is to average together all of the time profiles within a given ROI to form one vector of time responses. For ROIs that include spatial gradients, such as a cell membrane that demonstrates diffusion of a stimulus from its outer to inner boundaries over the time-span of the stimulus application, diffusion gradients could be calculated mathematically by measuring the differences between nearest-neighborhood data points from image to image over the time-span. This is similar to calculating a derivative via finite-differences. The diffusion pathway is identified as the chain of data points that exhibits the largest negative residual differences among subsequent image subtractions. For example, one subtracts the cell membrane ROI of image Ti+1 from image Ti. The data point with the largest negative magnitude in this residual image (which should be on the outer boundary of the membrane) will be the start of the diffusion gradient. Then one subtracts image Ti+2 from image Ti+1, and finds the data point with the largest negative residual that is close in space to the previous maximum residual points. This step is repeated for all of the remaining images up to Tf (or until the maximum negative residual "wave" has traversed the entire width of the membrane). Then, one calculates the rate of residual intensity transfer in units of distance/time across the width of the membrane. This procedure thereby results in a scalar quantity (diffusion rate) that is compared to, for example, stimulus magnitude or stimulus type. Furthermore, several such waves from different parts of the membrane can be calculated in order to determine an average diffusion rate. Note that several other quantities can be calculated for a set of images from different ROIs that exhibited different types of information (i.e., magnitude/static, spatial, and/or temporal). After calculating these values, they are then grouped into a single set of numbers (a vector) to represent the independent variables that are to be compared to a particular stimulus application.

The comparison may include elements of classification, regression, or qualitative procedures that are used to rank the data according to the applied stimuli. Such procedures define a model which, when applied to an independent variable vector collected on a sample stimulated in a similar manner in the future, yields a classification estimate or predicted stimulus magnitude. In addition, this procedure yields estimates of statistical quantities such as correlation coefficients for the independent vector components and confidence limits of, for example, a stimulus type classification estimate or stimulus magnitude estimate. An example of a classification type of comparison is to perform PCA on a collection of vectors calculated from several image sets that were exposed to different types of stimuli (e.g., sweet, bitter, salt). The PCA scores of this reduced data set clusters in the principal components space according to stimulus type. As an example of a quantitative regression application, the level of applied sweet stimulus in an unknown sample could be predicted using a multivariate correlation algorithm such as non-iterative Partial Least Squares (PLS). PLS is applied to a set of response vectors calculated from several applications of known levels of sweetness in order to construct a pattern of correlations between the calculated response vectors and their corresponding level of sweet stimulus. This pattern of correlations constitutes a mathematical model that can be applied to future response vectors in order to yield a prediction of applied sweetness.

It is understood that the examples and embodiments described herein are for illustrative purposes only and that various modifications or changes in light thereof will be suggested to persons skilled in the art and are to be included within the spirit and purview of this application and scope of the appended claims.

EXAMPLE 1

Multiphoton Fluorescence Lifetime Imaging System Characterization: Response to Calcium Green Dextran Solutions of Known Free Calcium Concentration The present inventors made use of a multiphoton lifetime fluorescence imaging microscopic (MP-FLIM) system capable imaging calcium dynamics within taste cells in intact, live porcine taste tissue. The approach made use of a calcium sensitive fluorescent dye (calcium green-1 dextran MW=3000), where the dye emission properties (fluorescence lifetime and intensity) were perturbed by intracellular calcium concentration changes in the nanomolar to millimolar range. Multiphoton-excited fluorescence, in this case, made use of a pulsed near-infrared laser to excite fluorescence from a visible fluorophore via a two or three photon process. This non-linear optical process allowed for deep tissue imaging of fluorophore emission with minimal cell damage from the near-infrared laser due to lack of absorption outside of the focal plane and absence of cytotoxic compounds that are generally formed as a result of photo degradation of dye molecules during standard ultraviolet calcium imaging.

The approach taken in this work made use of the changes in intracellular calcium concentration to indicate and quantitate the response of the gustatory system (taste bud) to stimuli. A key attribute of the MP-FLIM approach was the ability of the system to provide quantitative calcium concentration information from a calcium sensitive dye and its response to changes in free calcium ion in-vivo. In order to determine a quantitative relationship between stimulus and response, the response of the system to changes in bulk free calcium ion needed to be determined.

The inventors determined the relationship between the fluorescence lifetimes of a two-photon excited calcium green dextran dye and varying concentrations of free calcium in buffer. In addition, the effect of dye concentration in buffer was studied in order to determine if variations in cell loading would cause uncertainty in lifetime determination. Calcium green-1 dextran was chosen as the calcium sensitive dye for this work for the following reasons: (1) Calcium green-1 is a visible-light excitable calcium indicator (Ex. 505/Em. 532) with a KD for calcium in the appropriate range (~540 nM) for taste cell studies; (2) displays about a 100 fold increase in fluorescence intensity upon calcium ion binding; (3) has been used for measurements of relative changes in calcium (intensity) in taste cells in response to stimuli in rodents; and (4) a dextran-conjugated dye greatly reduces problems with sequestration of the dye in subcellular compartments and dye binding to cellular proteins. It also reduces transport of the dye out of the cell, which is a common problem in taste cells loaded with AM (membrane permeant) dyes.

Calcium buffers (CaEGTA) and calcium green-1 dextran (CaGD) were purchased from Molecular Probes. The calcium buffers provide free $Ca^{+2}$ over a nanomolar to millimolar concentration range in a matrix closely matching the pH and ionic strength of the cytosol. The lifetimes and relative contributions of these bound and unbound decays are determined by fitting multi-exponential curves to the instrumental data. Buffer kit #2 (0-39 micromoles/L free $Ca^{+2}$) was used in this work to determine the response of calcium green dextran to low calcium concentrations. Initial work was done with Buffer kit #3, but the range of free $Ca^{+2}$ (0-1000 micromoles/L) was too high for the dye chosen. Calcium ion concentration is approximately 0.1 micromoles/L in resting cell's cytoplasm and in the increases to the micromolar range upon stimulus (Pollard, 2002).

Samples were analyzed in a random order during each experiment using the MP-FLIM system and a quartz solution cell. Initial experiments were performed with 5-micromoles/L dye in the calcium buffer solutions, and these data are presented here first. Each sample produced two full fields of view (256×256) where each image pixel contains a decay curve. As the calcium green dextran was present in bound and unbound forms, double exponential fits were performed using SPCImage (version 2.7.7238.0). The double exponential decays were calculated for each sample on the entire field of view, generating 65,536 values for each field of view. The average decay for each field of view was calculated as a sum of the per pixel lifetime values weighted by the amplitudes (contributions) of each lifetime to each pixel. Table 1 details the results for the calculation of the unbound dye fluorescence lifetime. The average $\tau 1$ from the measurements is 405.6 ps, with a sample standard variance of approximately 1.0 ps.

TABLE 1

$Ca^{+2}$ results, calculation of short (unbound) lifetime component of the decay for calcium green dextran MW = 3000, 5 micromoles/L dye.

| Sample | Mean lifetime, $\tau$ ps | Mean unbound lifetime, $\tau 1$, ps | Standard deviation, $\tau 1$, ps |
|---|---|---|---|
| 0_a_1 | 617.8 | 403.3 | 144.1 |
| 0_a_2 | 603.6 | 405.5 | 109.3 |
| 0_b_1 | 623.0 | 406.9 | 95.7 |
| 0_b_2 | 619.1 | 404.4 | 90.85 |

The low standard deviation demonstrates the repeatability of the bulk measurement system for sample-to-sample averaged over the entire field of view. Individual samples exhibit an average $\tau 1$ variation of 109 ps per field of view, meaning the pixel to pixel variation under these fitting conditions is on the order to 109 ps. The balance of the calcium buffer data were analyzed using the SPCImage software under similar conditions as given in Table 1, with the exception that the short lifetime was fixed to 405.6 ps in the model parameters settings box. In addition, the zero $Ca^{+2}$ buffer average lifetimes were recalculated using the fixed short lifetime value. Due to instabilities in the software interface, the short lifetime was designated as $\tau 2$ in the fit parameters box. The average lifetime calculation results for the series of buffers are given in Table 2. A second order polynomial fit of average lifetime in picoseconds versus calcium concentration in micromoles/L for a calcium concentration range from 0 to 0.602 micromoles/L yields the relationship:

$$\tau_{avg} = -3047\ c^2 + 4472\ c + 601,\ R^2 = 0.9976;\ RMSE = 30.9\ ps.$$

TABLE 2

Average lifetimes calculated for each buffer, 4 fields of view per buffer, short lifetime fixed to 405.6 ps. The sample standard deviation is the standard deviation calculated from the average lifetimes from four fields of view. The pixel variability is a measure of variation within in a field of view. Dye concentration was 5 micromoles/L.

| Free Ca, micromoles/L | mean lifetime, ps | Std, sample variation, ps | Std, pixel variation, ps | Mean photon counts |
|---|---|---|---|---|
| 0.000 | 587.8 | 18.1 | 152.19 | 2042 |
| 0.017 | 653.0 | 4.6 | 103.77 | 2524.9 |
| 0.038 | 761.3 | 5.3 | 74.947 | 2846.8 |
| 0.065 | 880.9 | 7.1 | 52.66 | 3414.7 |
| 0.100 | 1068.6 | 8.7 | 58.68 | 3702.1 |
| 0.150 | 1215.6 | 28.4 | 44.02 | 4551.2 |
| 0.225 | 1463.2 | 25.2 | 48.03 | 5354.9 |
| 0.351 | 1750.4 | 15.2 | 59.69 | 6355 |
| 0.602 | 2200.8 | 25.8 | 51.77 | 7968.8 |
| 1.350 | 2841.9 | 4.9 | 46.31 | 10294 |
| 39.000 | 3081.9 | 3.0 | 82.27 | 13113 |

Figure 2:
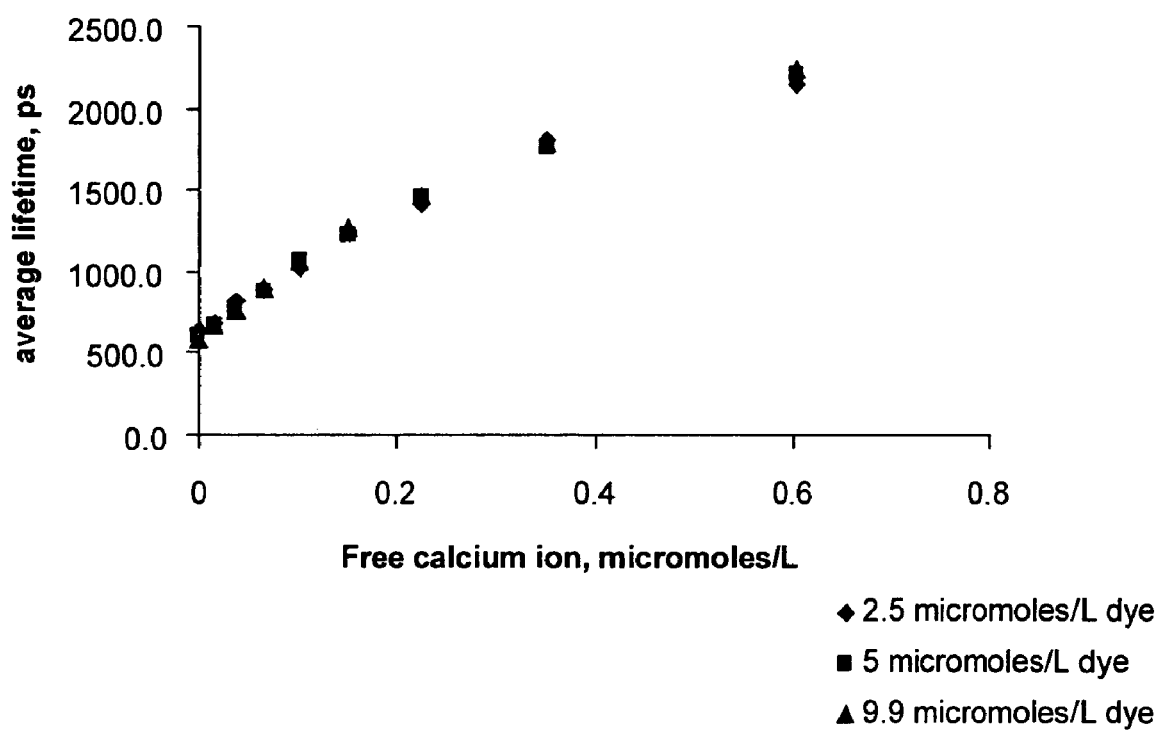
FIG. 2. Average fluorescence lifetime calculated from multiphoton lifetime fluorescence imaging (MP-FLIM) system as function of calcium concentration and dye concentration. Notice that the lifetime appears invariant, within experimental error, of dye concentration.
Figure 3:
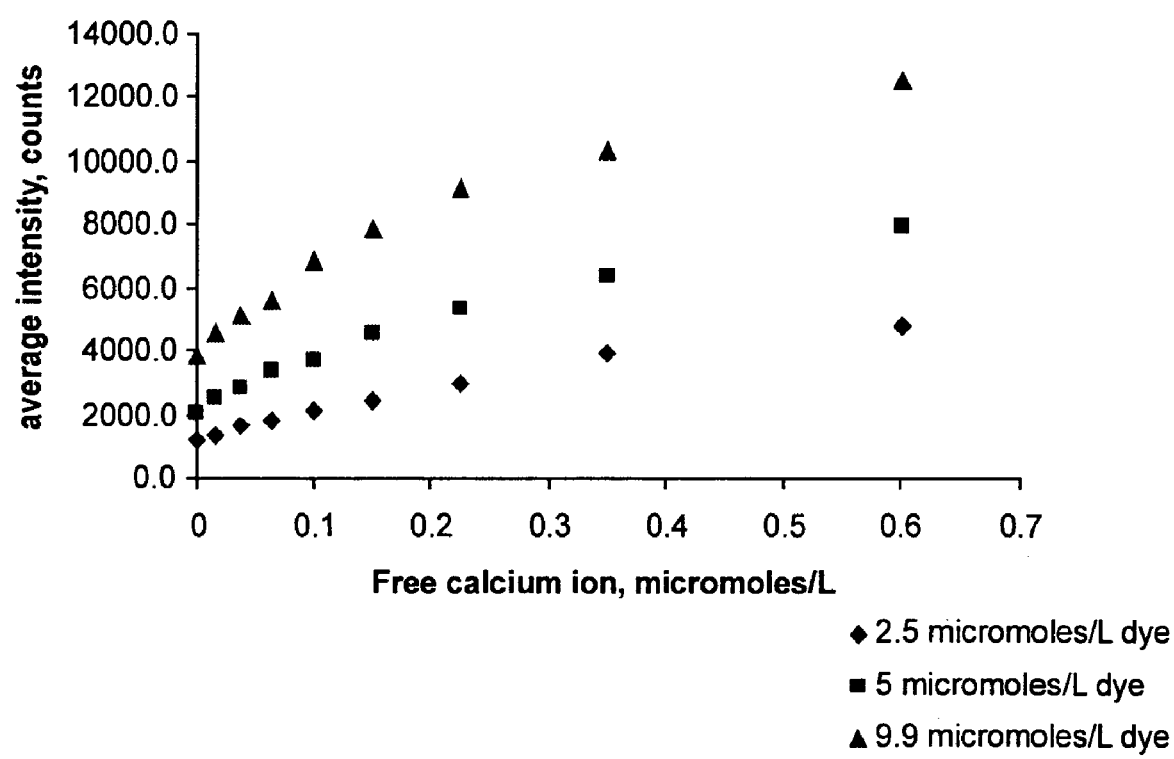
FIG. 3. Average fluorescence intensity measured using the MP-FLIM system as function of calcium concentration and dye concentration. Note that the emission intensity is a function of dye concentration and free calcium ion concentration.

A significant reported advantage of fluorescence lifetime measurements is that the dependence of fluorescence lifetime on calcium concentration is insensitive to dye concentration provided the dye itself is at low enough concentrations so as to not buffer the calcium ion in the cell or the cuvette. In order to test this property in the calcium green dextran system, additional sample sets were made up with 2.5-micromoles/L dye and 9.9-micromoles/L dye in the buffer solutions. The variations in lifetime data and intensity data with dye concentrations are given in FIG. 2 and FIG. 3, respectively. The lifetime data appears to be invariant with dye concentration, where the average standard deviation (variation in lifetime with dye concentration at each calcium concentration) for the lifetime data on the order or 25 ps. In contrast, the intensity variability is significant, where the intensity of the fluorescence is dependent upon the calcium concentration and the dye concentration.

Finally, calcium green-1 dissociation constants were calculated for the various dye concentrations using lifetime and intensity-based data sets. The Kd, or dissociation constant, of a chelator (indicator) is the binding constant for the complexation of the dye and calcium ion and is expressed in units of moles/L. The lifetime data exhibited a Kd standard deviation (n=3) of 27.3 mmol/L, and the intensity data exhibited a Kd standard deviation (n=3) of 71.4 nmol/L (see Table 3).

TABLE 3

Variation in dissociation constant with dye concentrations, Kd calculated based on intensity or lifetime data. The 2.5 and 9.9 micromole/L data were collected on Mar. 11, 2005, and the 5.0-micromole/L dye data were collected on Mar. 7, 2005. The intensity-based dissociation constant calculations from Mar. 11, 2005 exhibit greater variation than the values calculated from lifetime data.

| Dye concentration | Kd, nmol/L, Intensity Data | Kd, nmol/L, Lifetime Data |
|---|---|---|
| 2.5 micromoles/L | 482.5 | 342.0 |
| 5.0 micromoles/L | 520.1 | 329.1 |
| 9.9 micromoles/L | 382.0 | 289.5 |

The following observations and conclusions are made based on the calibration and characterization experiments detailed in this section. The MP-FLIM system provides reproducible fluorescence lifetime measurements of lifetimes ranging from <400 ps to >3000 ps, standard deviation of 25-30 ps. Calcium green dextran indicator fluorescence intensity and lifetime increase reproducibly with calcium concentration. The dissociation constant Kd for CaGD was calculated under various conditions using lifetime and intensity data and found to be consistent with that reported by the supplier (Molecular Probes, Inc.). The Kd ranged from 320 to 520 nM, with the lifetime determination providing a more reproducible Kd than that for the intensity-based method. For low micromolar indicator concentrations, fluorescence lifetime is independent of indicator concentration, while the fluorescence intensity depends significantly on indicator concentration.

EXAMPLE 2

Quantitative Algorithm Development and Estimation of System Optical Performance

There are a number of tasks involved to ensure precise and robust measurement of changes that occur in the image data obtained from the MP-FLIM system. First, an attempt should be made to mitigate artifacts induced by the optical path and detector on the "true" image data. In a spatially invariant system (i.e., all the pixels in the field of view experience the same optical and detector effects), such artifacts can be classified as either resolution loss (blurring) or recorded pixel intensity errors (noise). Second, because the image data are recorded in a flow cell, the image features may move over time, the process of image registration compensates for such movement by re-aligning the images in a given time-series with respect to a reference state (usually the first image in the series). Proper image registration is necessary when using region-of-interest (ROI) methods to quantify intensity changes in image features over time. Finally, an additional consideration in FLIM data is the fast and accurate calculation of lifetimes from the measured decays in each image pixel. Limitations in the currently used software included with the FLIM system will require incorporation of algorithms into MATLAB to perform these tasks alongside the artifact reduction routines mentioned above.

Estimation of System Optical Performance

An optical system is characterized by its Point Spread Function (PSF), which measures the effect on a point source of travel through the optical path and measurement by the optical detector. A PSF can be inferred from optical theory (usually assumed to be a symmetric Gaussian function), but a more accurate characterization can be done using fluorescent microspheres of known diameter. Collecting micrographs of isolated spheres under identical optical and environmental conditions as the sample to be studied results in a picture of how these variables affect a standard object. The size of the microsphere is known, and if it is small enough relative to the optical and digital resolution of the imaging system, it can be considered a homogeneous point source. Therefore, an image of this object can be treated as the actual PSF of the system (see FIG. 4).

The only further requirements of a PSF for use in calculations are that it preserves scale upon inversion (i.e., its elements sum to one), and that it is spatially invariant (i.e., it is plotted on a symmetric grid, with its center of mass in the exact center of the grid). In addition, background noise was subtracted from the microsphere image (so that "empty" pixels had a value of zero) and the central intensity feature was smoothed slightly to eliminate "roughness" due to detector noise. Because the original PSF image was taken at the highest resolution the highest resolution that the optical system was capable of (63× objective with hardware zoom of 20), this processed image was then down-sampled to match the conditions under which a particular sample image was collected prior to deconvolution. Deconvolution is the process by which the function of the optical system, as represented by the PSF, is removed from the sample image (see FIG. 5).

Quantitative Algorithm Development

Figure 6A:
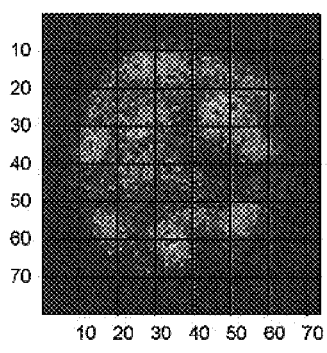
FIGS. 6A-6C. Preliminary deconvolution and denoising results. The Lucy-Richardson algorithm was used to perform the deconvolution using a slightly higher resolution version (3×) of the PSF shown in FIG. 5 above, along with noise parameters calculated from the microsphere data shown in FIG. 4 above to reduce noise amplification during the deconvolution process. This image was then denoised (i.e, smoothing "points" while preserving "edges") using an intensity gradient calculation method.
Figure 6B:
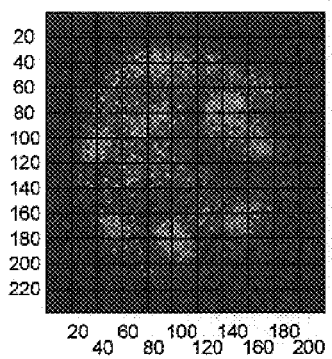
Figure 6C:
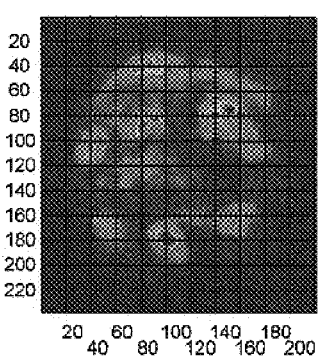

The Lucy-Richardson (L-R) algorithm was chosen as the means by which to deconvolve the PSF from the sample images. This algorithm is relatively fast and robust, and is considered "state-of-the-art" in the imaging community. The L-R routine employs certain "damping" parameters to help mitigate this; these parameters include the mean and variance of background noise (calculated from the microsphere images used to formulate the PSF) under assumptions of Poisson statistics (usually valid in "counting" experiments like digital imaging). However, so far it seems necessary to employ some of form of denoising (smoothing) along with the deconvolution in order to get the best possible feature resolution and noise elimination. A technique involving relative smoothing based upon intensity gradients works well at preserving "real" deconvolved features from amplified noise. As with the L-R algorithm, this method operates relatively quickly in MATLAB. This combination of deconvolution and denoising produces images that seems to make feature boundaries more distinct while reducing "speckle" (see FIG. 6).

Figure 7A:
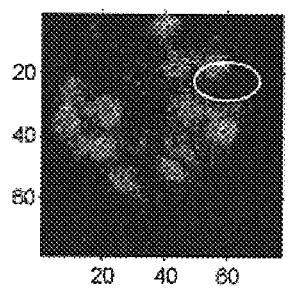
FIGS. 7A-7C. Example of time-series image stack registration. Note the considerable drift to the top and left of the taste bud over the course of the measurement (Unregistered #100) relative to its original position (Reference #1). The last image in the registered time-series stack (Registered #100) still shows some misalignment (note the position of the taste cell within the white ellipse in the 3 images).
Figure 7B:
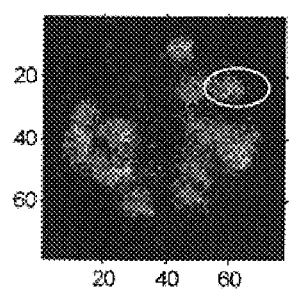
Figure 7C:
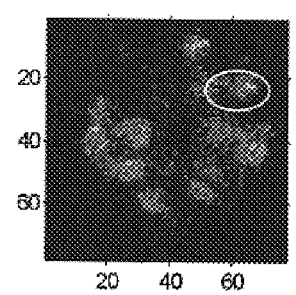

Aside from the instrumental artifacts, there are considerable movement artifacts in the image data. This problem of image registration is well known and can be effectively solved for many types of scale, perspective, and field of view differences between two images of the same scene. However, this robust approach requires a user to define reference points in each image that are used to construct spatial transformation matrix that is used to project the candidate image onto the axis space of the reference image. Since taste cell time-series usually consist of at least 100 images, this degree of user intervention is impossible. Therefore, image registration in this case must rely on "blind" iterative trials of coordinate shifts of each image in the stack relative to the first image. This process is actually fairly quick for stacks in which the maximum movement of a given image is less than 10 pixels in either direction, requiring perhaps 2 minutes to register a stack of 100 images (see FIG. 7) using a P4 2.8 GHz computer with 4 GB RAM.

Figure 8:
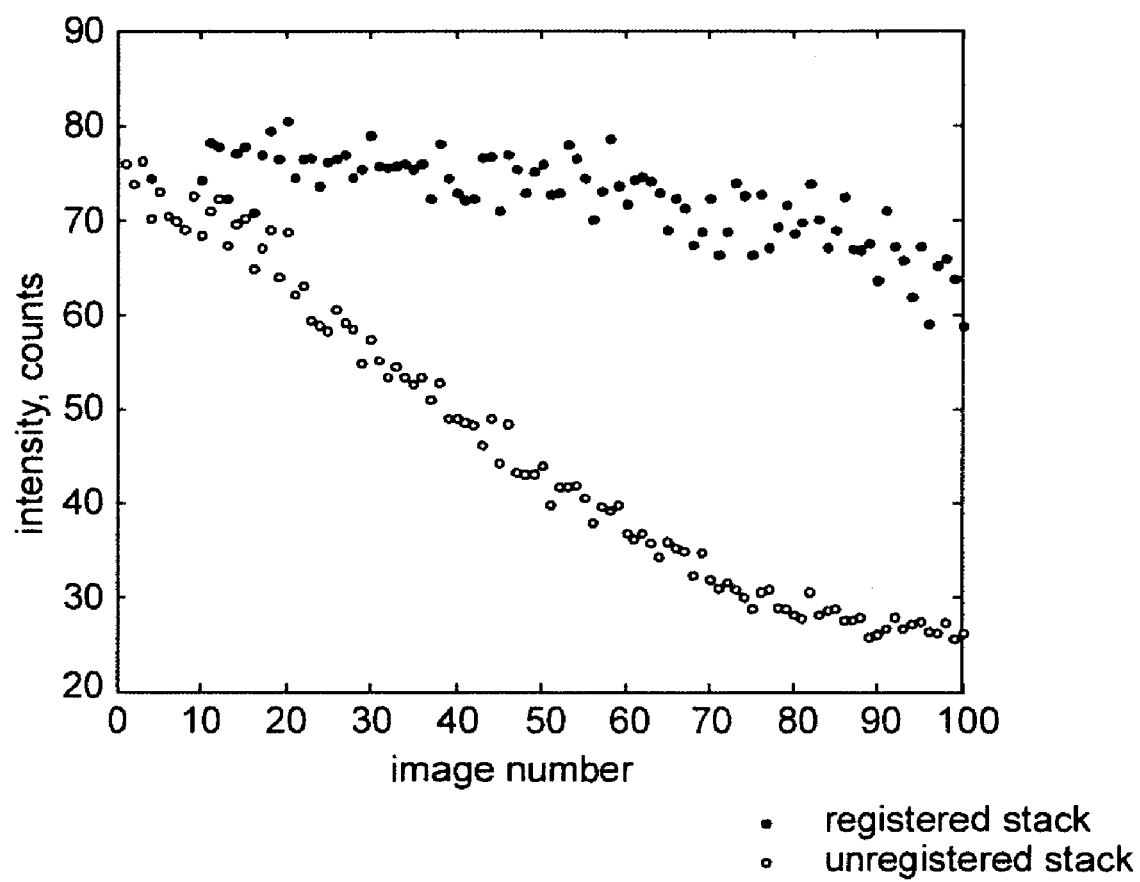
FIG. 8. Mean intensity trends of the region enclosed by the white ellipse in FIG. 7. Note the dramatic loss of intensity in the unregistered stack: this is due to the taste cell drifting outside of the ROI over time. There is some loss of intensity in the registered stack, but much of this is due to photobleaching (the overall intensity of the field-of-view of this data drops by ~10% over the course of the time-series).

Currently the registration process has some errors for images requiring large corrections (more than 10 pixels on an axis), but these are less than 5 pixels, and make ROI operations on individual features feasible (see FIG. 8). The errors are probably due to how the criterion for success is defined as well as real changes in feature intensity over a time-series stack.

While all of the above work applies to MP-FLIM as well as MP data, MP-FLIM data also requires determining the lifetimes of the fluorescent entities in an image as well as the relative intensity contributions of those lifetimes to each pixel in an image. So, for a 2-component system measured in a 256×256 image with 50 time points per pixel, there will be $256 \times 256 \times 3 = 1.97 \times 10^5$ parameters that need to be estimated over $3.7 \times 10^6$ data points. Without making any assumptions, this task requires several hours, and the results may be very inconsistent for low S/N data (as is often the case with MP-FLIM, especially in dynamic systems). Speed and/or accuracy of the solution can be greatly increased by using a priori lifetime values that are kept constant during the fitting, so that only the relative intensity contributions need to be fit (the so-called "lifetime invariant" approach). If these a priori lifetimes are accurate, and the instrument response function is accurately known, then incorporating these assumptions into an iterative fitting routine will give good, fast results. Even then, however, dramatic increases in speed can be found by segmenting the image into features based on binned intensity or very quick lifetime fits. This results in usually less than 10 features, which are then fit to yield initial lifetime and relative intensity estimates. Using these initial estimates, each pixel is then fit independently. These fits usually require far less iterations to converge, since the initial feature-based estimates are likely to be close to the final fitted value for all the pixels within a given region. In fact, this approach has been found to be comparable in speed and accuracy with the lifetime-invariant approach on high S/N images. In addition, it has been found to be equally accurate with only a moderate decrease in speed for low S/N images where the time invariant approach often converges to unrealistic parameter estimates (Pelet, 2004). Finally, since this feature segmentation requires user interaction at the start of the algorithm, the inventors of this approach show that an image division initialization produces fits that are somewhat slower and slightly less accurate, but that still yields reliable results for various image types while having the additional quality of being fully automated.

Calibration and Prediction Considerations

To establish a functional correspondence between type and concentration of stimulus as a dependent variable and taste bud response as an independent variable, the information in the MP & MP-FLIM images must be reduced into a set of variables that make up the input into a prediction equation to solve for either a stimulus type-response or a modifier perturbation response. Mathematically, the question is this: what will the various components of the regression equation $f(x)=y$ be? In a standard regression approach to what would be expected from initial stimulus-response experiments, y is a matrix consisting of between one and five quantities related to tastant concentrations in the stimulus solutions, x is a matrix of the measured features in the MP images, and "f" is the regression relationship between x and y. Ideally, f would be a linear combination of the x's, which would make the problem solvable by the widest variety of linear and linearizable techniques, e.g., PLS variants.

EXAMPLE 3

Development of Tissue Preparation Protocols

The utilization of porcine taste tissue in taste research is a new approach in taste research at the cellular level. Several researchers have performed behavioral studies with pigs (Kare, et. al, 1965) and one has performed electrophysiological recordings from nerve fibers and whole nerves innervating the peripheral taste system of pigs exposed to various stimuli (Danilova, 1999). These works provide a basis for the similarity between human and porcine taste responses, in bulk, but provide no knowledge regarding the anatomy and physiology of the porcine taste system. Therefore, the inventors embarked on a multi-faceted approach to develop knowledge of the porcine peripheral taste system in support of the project system development and the overall project goals of discovering taste modifiers.

In support of this work, microscopic assays were performed to ascertain the anatomy and physiology of the porcine taste bud system. These assays include: 1) Scanning electron microscopy for high-resolution surface anatomy of the taste structure; 2) Transmission electron microscopy for ultrastructural studies, including wide field microscopy through the sample preparation phase to assess tissue quality; 3) Immunocytochemical studies on fixed and prepared tissue section for determining the presence of specific classes of cellular machinery related to intracellular signaling and synaptic function; and 4) Multiphoton imaging of taste bud structures from tissue loaded with calcium sensitive dye, in this case calcium green dextran.

EXAMPLE 4

Electron Microscopy and Fixation Protocols

The inventors obtained high resolution scanning (SEM) and transmission electron (TEM) micrographs in order to determine the ultrastructure of the pig taste bud and surrounding tissue. This aided in the interpretation of the stimulus-response data to be obtained from the MP-FLIM system. Fixation of biological tissue and preparation for electron microscopy is complicated, so work began with a general mammalian fixative cocktail applied to small pieces of freshly obtained tissue. Each fixation trial used tissue for processing and imaging via light microscopy and electron (scanning and transmission) microscopy.

Initial inspection of the fixation results via the surface morphology of the papillae was performed by SEM. In most cases, a papilla from side of the tongue was used due to the slightly larger size of the papillae and the relative abundance of taste buds located in each. Many taste pores were observed scattered over the papilla surface and were noted by the morphology and topographic form. Also noted were the grooves discussed in literature as possibly being associated with assistance in guiding tastants to the taste pores. In several cases, multiple taste pores were noted within these grooves. In other cases, taste pores were noted as a depressed or raised structure. It was noted during SEM observations at higher magnification that few, if any, taste pores were located laterally to the papilla. Most taste pores are scattered across papillae dorsal surfaces.

It was difficult to develop a fixation protocol that would achieve acceptable preservation of the taste cells, supporting cells, and nerve processes when the test tissue was obtained from an abattoir. A general mammalian taste bud fixative from literature was attempted initially. The fixative cocktail was made up of some or all of the following in distilled water: paraformaldehyde, glutaraldehyde, sodium cacodylate, and sucrose. Modifications to the fixative concentrations and components were made in subsequent trials in order to improve the tissue quality under light microscope observation. In no case, with adult tissue, did the changes to the fixative cocktail result in properly preserved tissue. The tissue exhibited significant degradation, with gaps between cells and between the cytoplasm and nuclei of taste cells. In addition, the damage appeared, upon close inspection, to be pre-fixative in nature. Three trials were performed on the adult tissue, with variations in fixative composition and concentrations.

Subsequently, infant pig tissue from research pigs was obtained, and subjected to the fixative cocktail developed for the adult, killed pig tissue. This resulted in acceptable tissue preservation for TEM and yielded the first useful TEM images of porcine taste tissue. The infant tissue showed much better preservation, with no large gaps or voids between cells or cytoplasm and nuclei. The discovery that the tissue obtained from killed pigs is generally degraded prior to fixation indicated that the tissue may not be viable for a suitable period after slaughter. There are likely many reasons for this, including inflammation due to stress induced at slaughter, feeding and other care deficiencies, or time between slaughter and removal of the tongue.

EXAMPLE 5

Iontophoretic Loading of Taste Tissue with Calcium Green-1 Dextran

The inventors assessed the efficacy of the iontophoretic loading method for porcine taste tissue. Literature reports indicated successful loading of dextran conjugate dyes into rodent taste tissue (foliate papillae), but it was unclear if the process would be successful for pig fungiform papillae.

The fungiform papilla exhibited numerous pore structures on the surface of the tissue that were somewhat visible under moderate magnification using a specimen preparation epifluorescence stereomicroscope. Initial experiments were undertaken to optimize the loading of individual taste pores using a variety of glass pipette configurations and tip sizes for iontophoresis. Optimized loading parameters for individual pores were found to utilize Corning 7740 borosilicate glass (1.5 mm O.D.), pulled to a tip diameter of 4-6 μm, resulting in the most specific filling of taste cells and the least amount of damage to the tissue. This was accomplished for one pore at a time with 1-mmol/L dye in deionized water, 4-6 microamperes of current for 8-10 minutes.

In an effort to streamline the dye loading process, the inventors attempted to simultaneously load many taste buds in a single papilla using a fire-polished pipette with a tip just large enough to fit over a single fungiform papilla (0.8-1.5 mm). The initial experiments to load with a wide-bore capillary were successful in loading all accessible taste buds in subject taste papillae reproducibly. Again, the optimization procedure was applied using the wide-bore capillary. Optimal loading parameters were found to utilize 5-mmol/L dye, 200-300 microamperes of current, for 15 minutes of loading time.

The loading procedures were developed utilizing large (30 mm×15 mm) sections of lingual tissue excised from the tongues with minimal muscle and connective tissue retained on the tissue block. The first images obtained from the microscopic imaging system were captured from tissue immobilized onto a coverslip using tissue cement in a static pool of electrophysiological recording solution or artificial saliva. As the imaging system produces confocal images, three-dimensional models obtained for z-series image stacks were prepared from various loaded papilla under various conditions. Variability in tissue quality yielded mixed results in terms of number of cells per bud that loaded, and the number of buds loaded per papilla. In some cases, the presence of pores on the papilla surface was not an indicator of the presence of loaded taste buds under the pores, after iontophoretic loading. In these cases, the epithelial tissue surrounding the pore would load with dye but no fluorescence would originate from under the pore, indicating that either no taste buds were present or the apical ends of the taste cells did not extend into the pore, and thus the taste cells did not load with dye.

Post-load taste bud visualization was performed using a Leica TCS confocal microscopy system, and later using the visible laser line on the MP-FLIM system. Tissue was loaded with dye, one pore at a time, and then placed into an imaging chamber and imaged using the 488-nm excitation laser line and standard confocal optics in a z-series acquisition mode in order to generate an optically sectioned image stack for 3-D reconstruction. The images were maximum in plane projections, or three-dimensional reconstructions of the z-series data. Epithelial nuclei were clearly visible and appeared to have preferentially taken up dye, relative to dye uptake in the cytoplasm. Alternatively, the nuclei may contain significant unbound calcium ion, resulting in enhanced emission. The imaged cells were approximately 30-40 micrometers below the surface of the squamous epithelium and represent the practical limit for the interrogation depth by visible microscopy (1-photon excitation of the dye).

Upon complete installation of the MP-FLIM system the loading procedures were evaluated using the system in 2-photon excitation mode. The detector system was flexible enough that evaluations can be made using the descanned optical detectors, or through a higher efficiency non-descanned detector system. Initial multiphoton spectroscopic scans were performed with calcium green dextran dye solutions in order to determine maximum excitation efficiency for the dye under 2-photon excitation. Several high-resolution 3-dimensional datasets were collected over the course of the development work in order to provide insight into the loading efficiency and the types of cells that loaded. The data-sets were collected using the confocal descanned detector with a spectral window of 500-700 nm, pinhole open to 600 micrometers, 810 nm laser wavelength at 1.70 W indicated power, with 512×512 or 1024×1024 image sizes. The number of images collected per loaded bud depended on the level of dye loading to the basolateral membranes, but in general, 50-70 micrometers of total depth was imaged at 0.3 to 0.5 micrometers per z-slice. The apical and basolateral processes were clearly visible extending from the cell body. The differences in number of cells loaded between tissue samples may be related to any number of factors, including: tissue age, quality, developmental state of the papilla, and preferential loading of cell type.

EXAMPLE 6

Development of Stimulus Delivery System and Imaging Protocols

Imaging, Tissue Chamber, and Stimulus Delivery Systems

Initial characterization of the tissue loading and morphology was performed with pieces of tissue glued or cemented to a coverslip in an electrophysiological recording chamber. This approach was utilized with 40× and 63× water dipping objective lenses with laser power and wavelength optimized for the calcium green dextran. The mounting procedure was sufficient for evaluation of loading but did not provide a means for quantitative control of stimulus delivery and removal.

A commercially available temperature controlled isolated taste epithelium chamber was procured and utilized for mounting of an excised, dye loaded tissue block (5 mm×5 mm). This allowed isolation of the apical perfusion of stimulus delivery medium and the oxygenated basolateral perfusion medium. Initially, the chamber was used in the open configuration. The tissue was placed between the top plate and bottom plate of the chamber, forming a membrane between two separate perfusion baths. The chamber was sealed with high viscosity vacuum grease. The bottom perfusion of oxygenated Tyrode's solution was achieved with a peristaltic pump, initially, but this resulted in unacceptable pulsing of the tissue due to the pressure pulses induced from the peristaltic. The upper, open chamber was continuously perfused with artificial saliva via a gravity fed system. A constant volume was maintained in this chamber by removing solution with a syringe needle fixed at the appropriate level and attached to a vacuum line. An aliquot of stimulus was applied to the upper chamber from one of five 30 cc syringe barrels attached to a manifold via independently activated pinch valves. These reservoirs are pressurized if necessary. The system temperature is controlled to 30 degrees Celsius during stimulus experiments.

Due to control difficulties with the gravity feed liquid delivery system and peristaltic pump, modifications were made to the chamber design and pump system in order to confine the flow path, reduce the volume of perfusate in contact with the tissue, reduce pump noise, and reduce plugging in the chamber inlet and outlet lines. A push-pull pumping scheme for perfusates was designed and implemented for both perfusion chambers using dual Harvard Apparatus PhD syringe pumps and glass Gas-Tight syringes. These changes, coupled with Teflon tubing and finger-tight high performance liquid chromatography couplers, resulted in reproducible flow at relatively low rates (0.05 mL/min. to 1.00 mL/min) with minimal pressure pulse artifacts in the liquid stream. In addition, a remote controlled sample injection valve was ordered with variable injection loops available for introduction of stimulus into the fluidic system without reliance on gravity feed and pinch valves. Prior to receipt of the automated sample valve, a manual fixed volume (1.0 mL) valve was used to inject sample.

The flow characteristics of the system were measured using varying flow rates of upper perfusion with fluorescein visible dye in basic solution (pH=9). The dye was injected into the sample loop and time series intensity acquisitions made using the 2-photon mode in order to visualize the dye introduction and removal to and from the sample chamber close to the tissue position. The data were collected using the xzt mode of the microscope with the injection loop switched to "inject" mode at the onset of data acquisition. Because the dipping objective creates non-laminar flow regimes around the tissue, the profiles are not as uniform as would be expected. Likewise, variability in the bead size surrounding the objective was noted during flow experiments. However, the sample injection loop and syringe pump system provided improved sample injection integrity and flow stability relative to the gravity feed system. However, non-uniform flow characteristics of the open chamber coupled with the varying liquid bead size in contact with the objective lens resulted in irreproducible sample injection times as a function of flow rate. In addition, visual observation of the dye entrance, diffusion, and exit from the chamber showed that a preferred flow path in the chamber was around the objective close to the surface of the open bath. Therefore, the stimulus flow rate is necessarily coupled to diffusion in terms of stimulus exposure to the tissue. This coupling and bead variability precludes the accurate prediction of the arrival time of stimulus to the tissue surface.

Instability in the tissue during imaging experiments while using the flowing system led to a prolonged troubleshooting period where significant improvements were made in the tissue chamber design and the flow system as well as the mechanical stability of the microscope. It was apparent once the flow experiments were begun that the manual stage did not provide the mechanical stability required that would prevent movement of the stage once tubing and electrical connections were made to the epithelial chamber. Under static conditions, the stage was stable enough to allow for high-resolution three-dimensional imaging. However, the addition of fluid flow and variable mechanical load to the stage resulted in significant movement during stimulus and acquisition of image data. In some cases, the tissue would move 20-30 micrometers in 60 seconds, rendering any confocal imaging attempt useless. In order to stabilize the system, a computer controlled x-y stage was retrofitted to the microscope. This upgrade improved the stability of the system and allowed for continued troubleshooting of the residual movement issues that were attributable to flow instabilities and tissue mechanical response to stimuli.

The most recent series of tissue mounting and flow system modifications involved the conversion of the chamber to a gasket sealed closed chamber using a top coverslip, press-to-seal silicone gasket material, and a solid stainless steel pinhole substrate onto which the tissue was glued. The recent system optimization provided reproducible mounting and flow characteristics. The closed cell provided a uniform flow path, with no contact of the stimulus solution with the objective lens, thus providing additional stimulus timing stability as well as improving the tissue positional stability by removing the variable bead size atop the tissue in the flow cell. This improvement in the isolated epithelial chamber design improved the function and allows a single papilla to be placed in the chamber with reproducible mounting achievable. Finally, the closure of the flow cell results in the trapping of bubbles within the chamber. This results in compressible domains within the flow cell that produce pulses in the tissue position during switching of the sample injection valve. An ultrasonic vacuum degassing system was installed to provide bubble free perfusate solutions and reduce the bubble entrainment in the closed system.

EXAMPLE 7

Standard Taste Stimuli Selection and Refractive Index Matching to Perfusate

The choice of stimuli is driven by expectations for porcine response based on limited literature information as well as by practical experimental considerations. A significant challenge was encountered upon initial stimulus application using high concentration stimuli. The stimulus solutions were prepared in artificial saliva, initially, and exhibited significant refractive index variability, based on stimulus concentration. For a stimulus such as sucrose, the concentration threshold is high enough for humans that the refractive index perturbation relative to blank saliva is on the order of 0.01 refractive index units. This refractive index mismatch between stimulus and perfusate resulted in significant aberration and focal plane shift due to the perturbation of the optical path during bath application of stimulus. As the optical path comprises the objective, perfusion bath, and tissue for intact papilla imaging using an upright microscopic configuration, this level of refractive index mismatch is intolerable. For a typical slice preparation, the introduction of stimulus is achieved via a countercurrent application of stimulus from a micropipette positioned extremely close to the tissue and therefore stimulus does not perturb the imaging path. However, a slice preparation does not maintain the integrity of the taste bud and the polarization of the epithelium and for this reason we chose the bath stimulus system with intact papilla. It is probable that intensity-based calcium-imaging experiments reported in the literature that make use of bath stimulus might contain artifacts related to refractive index perturbations arising from stimulus-perfusion bath mismatch.

As the intact papilla is the preferred tissue sample type for this work, refractive index matching of the stimulus and perfusion bath solutions was pursued. Taste-free, water soluble, low viscosity carboxymethylcellulose was procured from Sigma Aldrich in powder form to be used as a refractive index perturber. Solutions of stimuli were prepared in artificial saliva, initially, and the refractive index at 546 nm measured using a handheld refractometer. It was determined that a refractive index mismatch of 0.0003 refractive index units was sufficient to produce focus shifts and image distortions in the perfusion bath. Subsequently, a stock solution of CMC was prepared in deionized water or saliva having a refractive index on the order of 1.3400. From dilutions of this stock solution, a calibration curve was developed relating CMC by weight in solution to the refractive index. Index matched stimulus solutions were prepared using the CMC calibration and adjusted dropwise to within ±0.0001 RI units of the target. In general, the most concentrated stimulus solution in a set of stimuli was chosen as the target for RI matching. This method was successfully applied to solutions prepared in deionized water and in artificial saliva and, in general, produced little to no refractive index artifacts in the image data.

EXAMPLE 8

Multiphoton Fluorescence Intensity and
Lifetime-based Response of Porcine Taste Tissue:
Preliminary Lifetime Imaging of Stimulated Tissue
in Static Bath Fresh porcine taste tissue was procured in the prescribed manner from a local slaughterhouse and transported, after removal from the tongue, in chilled, oxygenated Tyrode's solution to the preparation laboratory. The tissue was affixed to a coated Petri dish and taste buds iontophoretically loaded (1.0 microampere) with calcium green dextran dye (1 mmol/L in DI water) via a drawn capillary pipette. Several taste pores were loaded on a papilla, with several papillae loaded overall, providing 3-5 taste buds loaded with dye. The tissue was mounted in a chamber and placed onto the microscope stage. The sample was imaged using the 63× water-dipping objective, 60% laser power at 810-nm excitation, in xzy mode (256×256 pixels) in order to image the taste bud and surface features at once in a longitudinal section. The photomultiplier tube gain on the FLIM system was set to 85% and the initial Leica settings (non-optimized) were used to capture FLIM images of the tissue over a 10-15 minute time course.

The same field of view was then imaged using the multiphoton lifetime imaging capability of the instrument. The optical conditions for lifetime mage collection are identical to intensity-based imaging, except that in photon counting mode the collection requires 30 seconds in this case for adequate signal to noise. The lifetimes were calculated by a double exponential fit of the decay curves and color-coded based on average lifetime per pixel. Red values are shorter lifetimes in this case. The epithelial cells (surface cells), which load with dye, exhibit, on average, longer lifetimes than the taste cells located below the pore. The shortest lifetime evident in this image is associated with the apical end of the taste cell directly below the pore. At rest, the average lifetime for all of the cells in the field of view is 1,634 picoseconds. The short lifetime component of the fit was set to 350 picoseconds, an estimate of the short lifetime component based on initial calcium calibrations in order to facilitate rapid fitting of the data for comparison.

Figure 9:
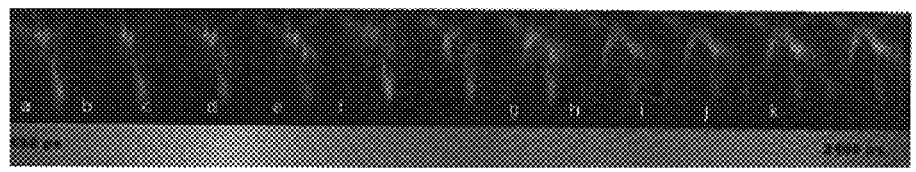
FIG. 9. Time series multiphoton image of taste bud region during stimulus with cycloheximide and sucralose. a) rest; b) cycloheximide addition; e) refocus f) sucralose stimulus. Notice that the sucralose stimulus results in significant shortening of the calcium green lifetime around the taste cells. As the calcium green lifetime associated with the epithelial cells remains essentially unchanged during the experiment, it is clear that he taste cells responded to the stimuli.

The taste bud was exposed to several gross stimuli: cycloheximide and sucralose in deionized water. The purpose of this stimulus experiment was to determine if the bud would remain viable during the time course of a stimulus and if possible, to determine the presence of a gross response via lifetime imaging. The stimulants were applied via bulk addition to the chamber holding the tissue: 0.5 mL of 25-micromolar cycloheximide was first added after removal of 1 mL buffer; 0.5 mL of 1-millimolar sucralose added after the cycloheximide stimulus and removal of additional 1 mL buffer. The MP-FLIM image data were collected at approximately 1-minute intervals using the same optical and exposure conditions used to generate the resting image described above. FIG. 9 shows the representative color-coded average lifetime images for the sequence of images captured during exposure to the different stimuli. The letters in the image correspond to subsequent sub-images collected during the experiment: a) rest; b) cycloheximide addition; e) refocus f) sucralose stimulus. Notice that the sucralose stimulus results in significant shortening of the calcium green lifetime around the taste cells. As the calcium green lifetime associated with the epithelial cells remains essentially unchanged during the experiment, it is clear that the taste cells responded to the stimuli. It is clear that the calcium concentration surrounding the taste cells decreased during exposure to the sucralose stimulus, and in addition, color changes associated with calcium green lifetime changes are evident in cells not originally imaged in the cells at rest.

EXAMPLE 9

Multiphoton Fluorescence Intensity-based Response
of Porcine Taste Tissue: Preliminary Imaging of
Stimulated Tissue in Flowing Perfusing Medium Tissue was received from the abattoir and loaded with calcium green-1 dextran using the optimized wide-bore loading method: 300 microamperes for 15 minutes. Two papillae in close proximity to one another were loaded in this manner. The papillae were extracted from the larger piece of tissue and placed into the open chamber configuration (this work was done prior to that using the closed, gasketed chamber). The tissue was repeatedly stimulated with 20 mmol/L citric acid using the 1.0 mL/min flow rate and 1.0 mL sample loop, switched to the load position as time series data acquisition began. The imaging parameters were as follows: 400 Hz galvo scan rate, 2× zoom with 63× objective, 256×256 pixel image format, 2× frame average, 810 nm laser at 36%, and 0.5 Hz frame scan rate. The tissue was received at approximately 8:00 am, transported in oxygenated Tyrode's solution to the lab, loaded at approximately 10:00 am and imaged at approximately 11:00 am.

Figure 10A:
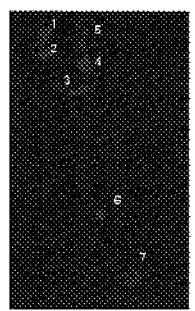
FIGS. 10A and 10B. Image field of view showing the two taste buds with several cells in each loaded with dye (FIG. 10A). The stimulus application resulted in intracellular calcium increase in cell 1 and possibly cell 2 (FIG. 10B). However, the slope and baseline offset between cells make it difficult to compare responses. However, the alignment algorithm allowed individual cell ROI's to be defined for time series analysis.
Figure 10B:
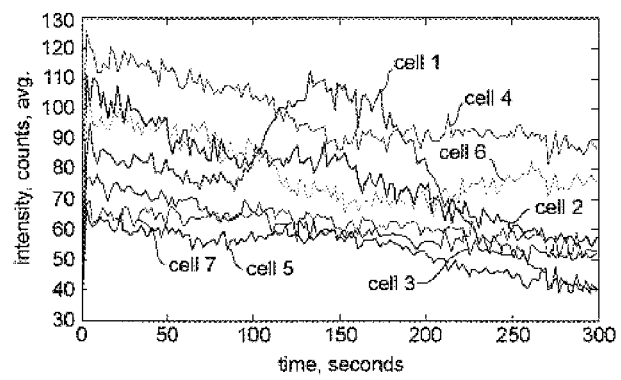

Cells from two adjacent taste buds within the second papilla were imaged in xyzt mode at a depth of approximately 35 micrometers. Five cells from the upper taste bud and two cells from the lower bud appeared to load well with dye. (See FIG. 10). The time series data were processed using the alignment tools development to address the tissue movement issues. An important point to be made here is the reproducible movement witnessed during numerous citric acid stimuli. The acid stimulated movement is not an artifact of the flow cell or due to stage instability; it is truly a mechanical response to a change in pH. However, the movement in this case was primarily in the x-y plane, and therefore the alignment algorithm provided sufficient alignment.

It was noticed that several of the cells showed relative increases in average intensity, indicative of an intracellular increase in calcium ion concentration. In most cases where movement was the dominant perturbation in the image data, the movement is monotonic. However, it was clear that adjacent cells in the examined bud exhibit significant intensity changes corresponding to the acid stimulus.

Figure 11A:
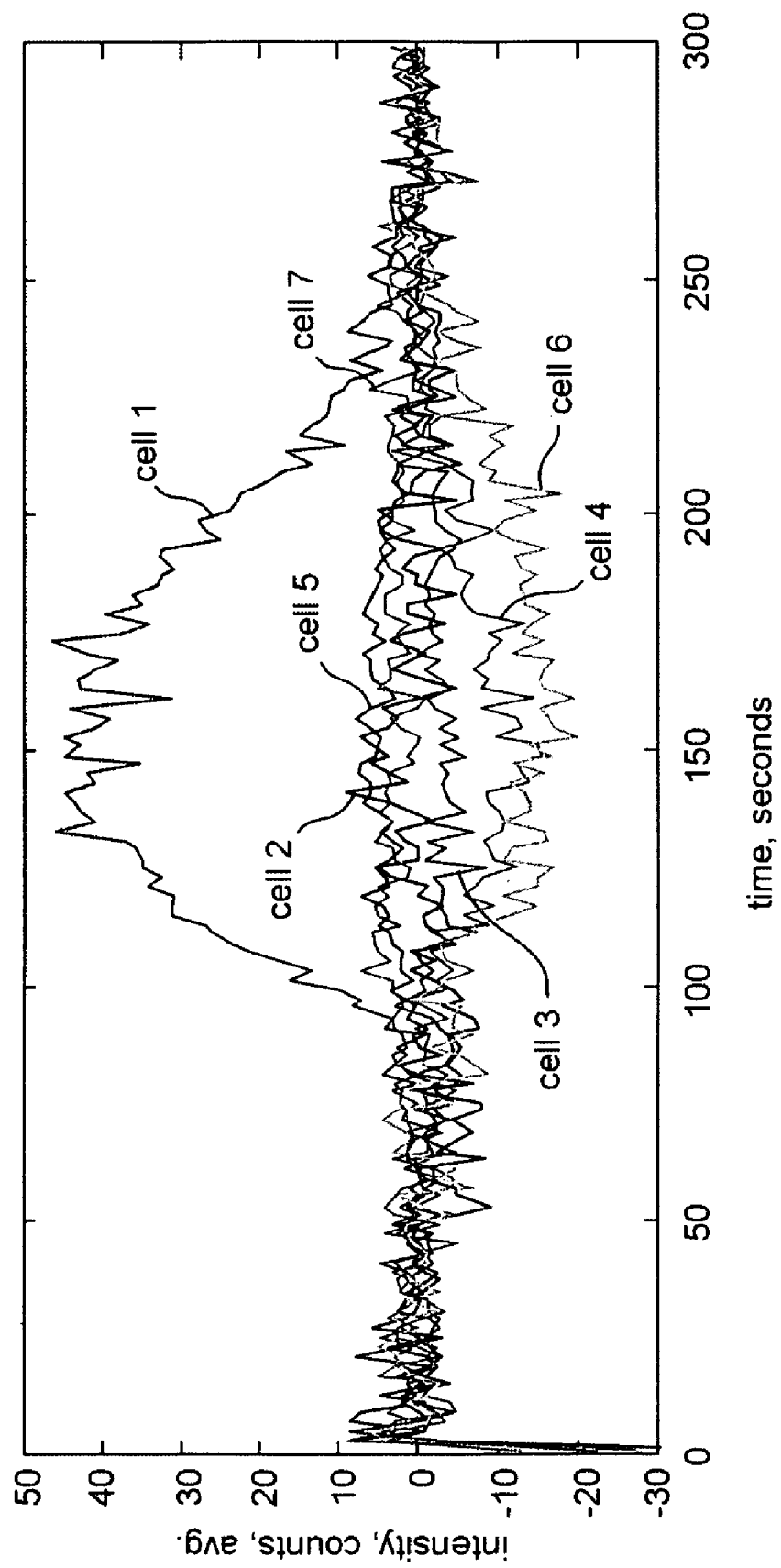
FIGS. 11A-11C. Baseline corrected time series data for all seven cells in the field of view during successive 20 mmol/L citric acid stimuli. The taste buds were exposed to artificial saliva (no stimulus) for 5 minutes between stimuli to allow for recovery. Note the strong response to the stimulus in cell 1 with lower magnitude responses in other cells. The decrease in response to subsequent stimulus is most likely due to the lack of viability of the tissue or to adaptation.
Figure 11B:
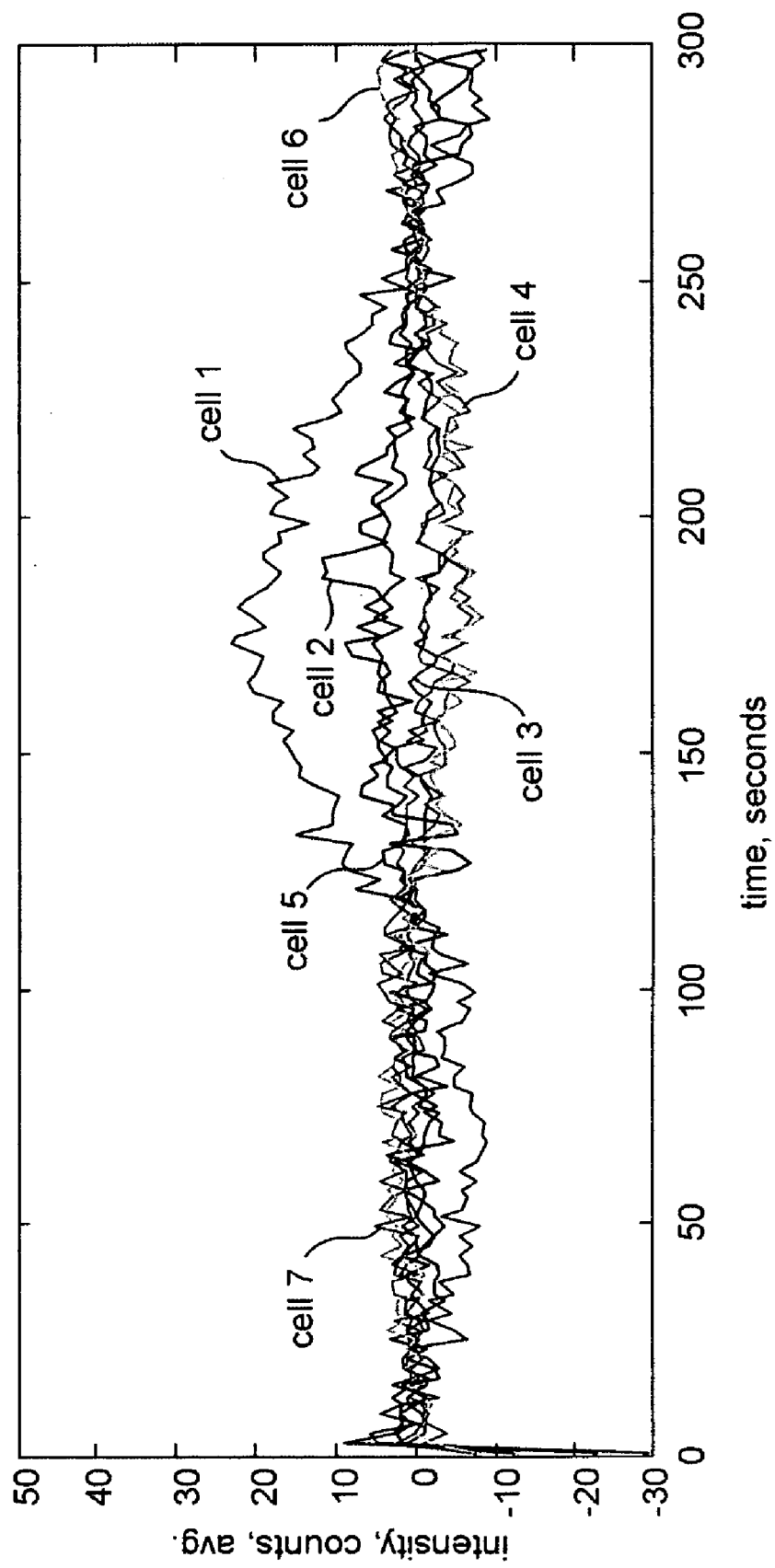
Figure 11C:
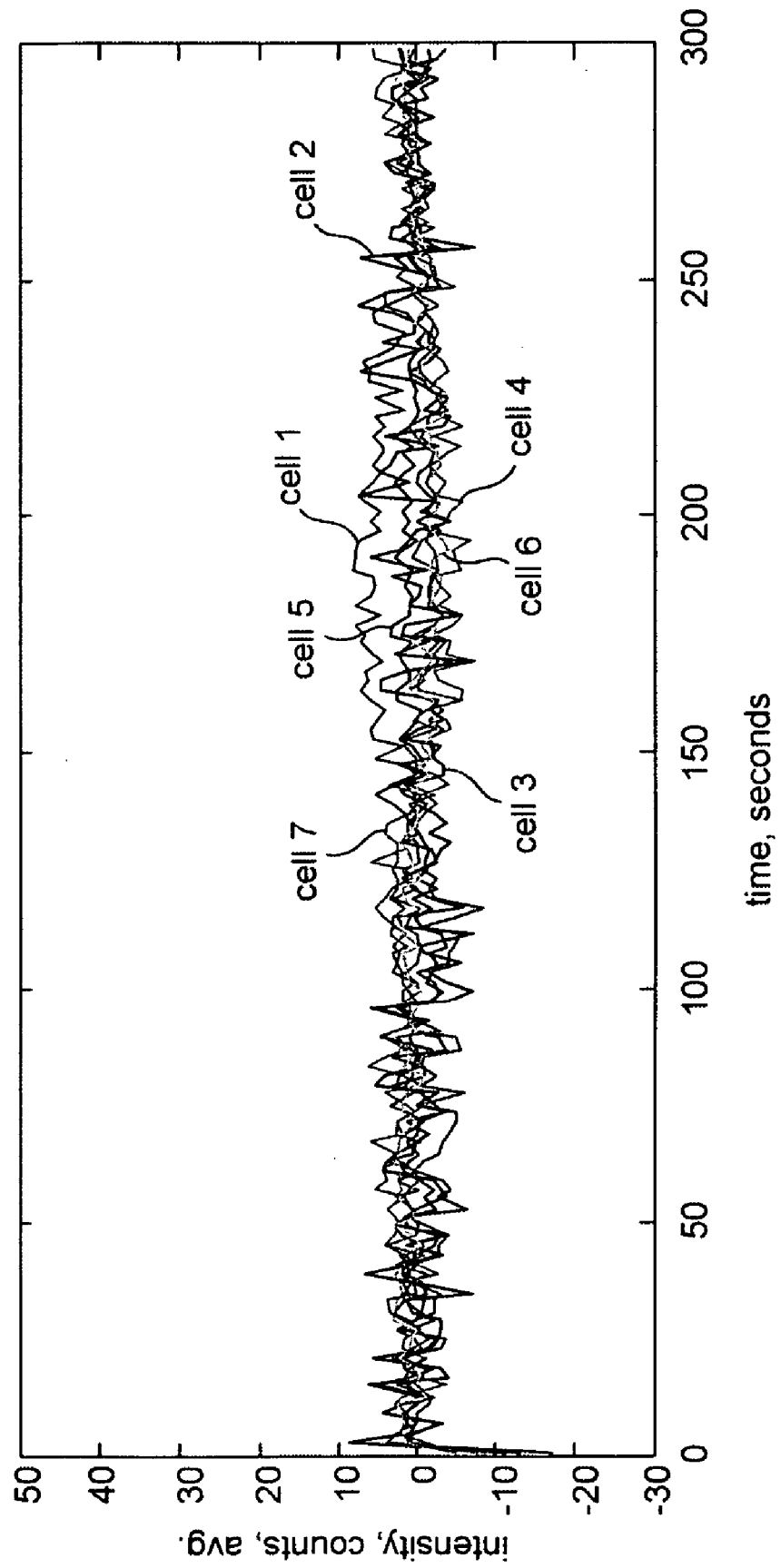

Time series data show distinct stimulus-related changes in the relative emission intensity for several cells. However, the relative difference in emission and differences in slope due to photobleaching makes comparison between cells difficult. Therefore, a baseline correction was applied to the time series data to remove offset and slope differences between traces. The response decreased in magnitude with subsequent stimulus, an indication that the tissue was reaching the end of viability (see FIG. 11). Given the time between slaughter and exposure to stimulus (4 hours) it is not surprising that the tissue appeared to be dead or dying.

It was also noticed that other cells appeared to minimally respond to successive stimuli with slight increases in average fluorescence intensity, and other cells in the system respond with a slight decrease in fluorescence intensity. The differential responses of different cells in the buds may be attributable to either intercellular trafficking of calcium ion, evidence of cell-to-cell communication in response to a single cell-signaling event due to taste receptors. Conversely, taste receptor cells may respond by either excitatory (increase in intracellular calcium) or inhibitory (decrease in intracellular calcium) activity.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

REFERENCES

Ashworth, R. *Approaches to measuring calcium in zebrafish: focus on neuronal development*, Cell Calcium 35 (2004) 393-402.

Baryshnikov et al. 2003. J. Neurophysiol. 90:3283

Boudreau, J. C. and N. Alev. 1973. *Classification of chemoresponsive tongue units of the cat geniculate ganglion*. Brain Res. 54:157-175

Boudreau, J. C. and T. E. Nelson. 1977. *Chemical stimulus determinants of cat geniculate ganglion chemo-responsive group I discharge*. Chem. Senses Flavour. 2:353-374

Boudreau, J. C., Bradley, B., Bierer, P., Kruger, S. and C. Tsuchitani. 1971. *Single unit recordings from the geniculate ganglion of the facial nerve of the cat*. Exp. Brain Res. 13:461-488

Boudreau, J. C., Sivakumar, L., Do, L. T., White, T. D., Oravec, J. and N. K. Hoang. 1985. *Neurophysiology of geniculate ganglion (facial nerve) taste systems: species comparisons*. Chem. Senses. 10:89-127.

Bourne, J. and J. C. Kinnamon. 1999. *Co-localization of serotonin-like immunoreactivity with synaptic proteins in taste buds of rat*. Chem. Senses. 24:589.

Brand, J. H., Teeter, J. H., Kumazawa, T., Huque, T., and Bayley, D. L. 1991. *Transduction mechanism for the taste of amino acids*. Physiol. Behav. 49: 899-904;

Caicedo, A., Jafri, S, and Roper, S. D., 2000, *In Situ Ca Imaging Reveals Neurotransmitter Receptors for Glutamate in Taste Receptor Cells*, The Journal of Neuroscience, November 1, 20(21):7978-7985.

Caicedo, A., Kim, K. N. and S. D. Roper. 2002, *Individual mouse taste cells respond to multiple chemical stimuli*. J. Physiol. 544.2:501-509.

Caprio, J. 1975. *High sensitivity of catfish taste receptors to amino acids*. Comp. Biochem. Physiol. A. 52:247-251

Clapp, T. R., Yang, R., Stoick, C. L., Kinnamon, S. C. and J. C. Kinnamon. 2003. *Morphological characterization of rat taste receptor cells that express components of the phospholipase C signaling pathway*. J. Comp. Neurol. 468:311-321.

Danilova et al., 1999, *Responses of single taste fibers and whole chorda tympani and glossopharyngeal nerve in the domestic pig, Sus scrofa*. Chemical Senses, 24:301-316.

Delay, R. J., Kinnamon, J. C. and S. D. Roper. 1986. *Ultrastructure of mouse vallate taste buds. II. Cell types and cell lineage*. J. Comp. Neurol. 253:242-252.

Finger T. E., Simon S. A., 2000, *Cell biology of taste epithelium. In: The neurobiology of taste and smell, Ed 2* (Finger T E, Silver W L, Restrepo D, eds), pp 287-314. New York: Wiley.

Finger, T. E., Bryant, B. B., Kalinoski, D. L., Teeter, J. H., Böttger, B., Grosvenor, W., Cagan, R. H. and J. G. Brand. 1996. *Differential localization of putative amino acid receptors in taste buds of the channel catfish, Ictalurus punctatus*. Journal of Comparative Neurology. 373: 129-138

Finger, T. E. and S. A. Simon. 2000. *Cell biology of taste epithelium*. In: Finger, T. E., Silver, W. L. and Restrepo, D., eds. The neurobiology of smell and taste, New York, Wiley-Liss. Pp. 287-314.

Finger, et al., ATP *Signaling Is Crucial for Communication from Taste Buds to Gustatory Nerves* Science 2 Dec. 2005: 1495-1499

Fugimoto, S., Ueda, H. and H. Kagawa. 1987. *Immunocytochemistry on the localization of 5-hydroxytryptamine in monkey and rabbit taste buds*. Acta Anat. (Basel). 128: 80-83.

Gratton, E., Breusegem, S., Sutin, J., Ruan, Q. and N. Barry. 2003. *Fluorescence lifetime imaging for the two-photon microscope: time-domain and frequency-domain methods*. J. Biomed. Optics 8:381-390;

Hayashi, Y., M. M. Zviman, J. G. Brand, J. H. Teeter and D. Restrepo. 1996. *Measurement of membrane potential and $[Ca^{2+}]_i$ in cell ensembles: Application to the study of glutamate taste in mice*. Biophysical Journal. 71: 1057-1070;

Herness et al., 2005, "*Communication Routes within the Taste Bud by Neurotransmitters and Neuropeptides,*" Chemical Senses Kare, M. R., Pond, W. C., and Campbell, J. *Observations on the taste reactions in pigs*, Animal Behaviour, XIII, 2-3, 1965.

Kim, D-J. and S. D. Roper. 1995. *Localization of serotonin in taste buds: a comparative study of four vertebrates*. J. Comp. Neurol. 353:364-370.

Kinnamon, J. C., Taylor, B. J. Delay, R. and S. D. Roper. 1985. *Ultrastructure of mouse vallate taste buds. I. Taste cells and their associated synapses*. J. Comp. Neurol. 235:48-60.

Kinnamon, J. C., Sherman, T. A. and S. D. Roper. 1988. *Ultrastructure of mouse vallate taste buds. III. Patterns of synaptic connectivity*. J. Comp. Neurol. 270:1-10.

Kinnamon, J. C., Henzler, D. M. and S. M. Royer. 1993. *HVEM ultrastructural analysis of mouse fungiform taste buds, cell types, and associated synapses*. Microsc. Res. Techniq. 26:142-156.

Koester, H. J., Baur, D., Uhl, R. And S. W. Hell. 1999. $Ca^{2+}$ *fluorescence imaging with pico- and femtosecond two-photon excitation: signal and photodamage*. Biophys. J. 77:2226-2236;

Konig, K. et al. 1997. *Cell damage in UVA and CW/femtosecond NIR microscopes*. SPIE vol. 2983:37-44;

Krimm, R. F. and D. L. Hill. 1998. *Innervation of single fungiform taste buds during development in rat* J. Comp. Neurol. 398:13-24;

Kumazawa T. and K. Kurihara. 1990. *Large synergism between monosodium glutamate and 5'-nucleotides in canine taste nerve responses*. Am. J. Physiol. 259:R420-R426

Kumazawa T., Kurihara K. 1990. *Large enhancement of canine taste responses to sugars by salts*, J. Gen. Physiol. 95:1007-1018

Kumazawa T., Nakamura M., Kurihara K. 1991. *Canine taste nerve responses to umami substances*. Physiol. Behav. 49:875-881

Lakowizc, J. R., *Principles of Fluorescence Spectroscopy*, $2^{nd}$ *Edition*, 1999, Kluwer Academic/Plenum Publishers.

Lindemann, B., 1996, *Taste reception*, Physiol. Reviews, 76:718-766

Liu, D. and E. R. Liman. 2003. *Intracellular Ca$^{2+}$ and the phospholipids PIP$_2$ regulate the taste transduction ion channel TRPM5*, 2003. PNAS 100:15160-15165.

Lyall et al., Chem. Senses 30:i42 (2005)

Lyall et al., 2004, *The mammalian amiloride-insensitive non-specific salt taste receptor is a vanilloid receptor-1 variant*. J Physiol. 558(Pt 1): 147-59.

Medler, K. F., Margolskee, R. F. and S. C. Kinnamon. 2003. *Electrophysiological characterization of voltage-gated currents in defined taste cell types of mice*. J. Neurosci. 23:2608-2617.

Murray, R. G. 1973. The ultrastructure of taste buds. In: Friedemann, I., ed., *The ultrastructure of sensory organs*. Amsterdam. North Holland, pp. 1-81.

Nakamura M., Kurihara K. 1990. *Non-specific inhibition by amiloride of canine chorda tympani nerve responses to various salts: do Na$^+$-specific channels exist in canine taste receptor membranes?*. Brain Res. 524:42-48;

Nakamura M., Kurihara K. 1991. *Canine taste nerve responses to monosodium glutamate and disodium guanylate: differentiation between umami and salt components with amiloride*. Brain Res. 541:21-28.

Nelson, G. M. and T. E. Finger. 1993. *Immunolocalization of different forms of neural cell adhesion molecule (NCAM) in rat taste buds*. J. Comp. Neurol. 336:507-516.

Pelet, S., Previte, M. J. R., Laiho, L. H., and So, P. T. C. *A Fast Global Fitting Algorithm for Fluorescence Lifetime Imaging Microscopy Based on Image Segmentation*, Biophysical Journal, 87: 2807-2817).

Pollard and Earnshaw, Cell Biology, Saunders, 2002 Roper et al., 1989, *Ann. Rev. Neurosci.* 12:329-353

Reutter, K. 1971. Die Geschmacksknospen des Zwergwelses Ameiurus nebulosus. Morphologischische and histochemische Untersuchungen. Z. Zellforsch. 120:280-308.

Reutter, K. and M. Witt. 1993. *Morphology of vertebrate taste organs and their nerve supply*. In: Simon, S. A. and Roper, S. D., eds. Mechanisms of taste transduction. Boca Raton, Fla. CRC Press, pp. 29-52.

Royer and Kinnamon, 1991, *HVEM serial-section analysis of rabbit foliate taste buds: I. Type III cells and their synapses*. J Comp Neurol.306(1):49-72.

Royer, S. M. and J. C. Kinnamon. 1994. *Application of serial sectioning and three dimensional reconstruction to the study of taste bud ultrastructure and organization*. Microsc. Res. Techniq. 29:381-407.

Takeda, M. and T. Hoshino. 1975. *Fine structure of taste buds in the rat*. Arch. Histol. Jpn. 37:395-413.

Uchida, T. 1985. *Serotonin-like immunoreactivity in the taste bud of the mouse circumvallate papilla*. Jpn. J. Oral boil. 27:132-139.

Witt and Reutter, 1996 *Embryonic and early fetal development of human taste buds: a transmission electron microscopical study*. Anat Rec. 246(4):507-23.

Yee, C. L., Yang, R., Bottger, B, Finger, T. E. and J. C. Kinnamon. 2001. *"Type III" cells of rat taste buds: immunohistochemical and ultrastructural studies of neuron-specific enolase, protein gene product 9.5, and serotonin*. J. Comp. Neurol. 440:97-108.

Yee, C. L., Jones, K. R. and T. E. Finger. 2003. *Brain-derived neurotrophic factor is present in adult mouse taste cells with synapses*. J. Comp. Neurol. 459:15-24.

Yang, R., Crowley, H. H., Rock, M. E. and J. C. Kinnamon. 2000. *Taste bud cells with synapses express SNAP-25-like immunoreactivity*. J. Comp. Neurol. 424A:205 215.

Yang, R., Stoick, C. L. and J. C. Kinnamon. 2004. *Synaptobrevin-2-like immunoreactivity is associated with vesicles at synapses in rat circumvallate taste buds*. J. Comp. Neurol. 47:59-71.

Zviman, M. M., D. Restrepo, and J. H. Teeter. 1996. *Single taste stimuli elicit either increases or decreases in intracellular calcium in isolated catfish taste cells*. Journal of Membrane Biology. 149: 81-88.

What is claimed is:

1. A method for determining a functional cellular response of an isolated taste cell or taste cells from an animal to one or more test stimuli comprising:
   a) isolating a lingual epithelium containing intact taste-buds in an intact papilla wherein said lingual epithelium has a basolateral surface and an apical surface;
   b) mounting said lingual epithelium in a chamber to allow separate solutions to independently perfuse said basolateral and apical surfaces of said lingual epithelium;
   c) perfusing said basolateral surface with a first solution and said apical surface with a second different solution;
   d) contacting said apical surface with a stimuli through said first solution;
   e) quantitatively determining a magnitude of at least one functional cellular response from said lingual epithelium initiated by said stimuli.

2. The method of claim 1, wherein the taste-bud containing lingual epithelium comprises a detectable moiety.

3. The method of claim 2, wherein the detectable moiety is detectable by spectroscopic, photochemical, biochemical, immunochemical, physical, or chemical means.

4. The method of claim 2, wherein the detectable moiety is a fluorescent dye, an electron-dense reagent, an enzyme, biotin, digoxigenin, or a hapten or a protein that has been made detectable.

5. The method of claim 2, wherein the detectable moiety is a calcium-sensitive dye.

6. The method of claim 5, wherein the calcium-sensitive dye is Calcium Green.

7. The method of claim 2, wherein the detectable moiety is a voltage-sensitive dye.

8. The method of claim 1, wherein the taste-bud containing lingual epithelium is obtained from a eukaryotic organism.

9. The method of claim 8, wherein the eukaryotic organism is a mammal.

10. The method of claim 9, wherein the mammal is a rat, mouse, cat, cow, dog, pig, rabbit, chimpanzee, or human.

11. The method of claim 9, wherein the mammal is a pig.

12. The method of claim 1, wherein the taste cell or cells have an apical surface and a basal surface, wherein the stimuli contacts the apical surface of the taste cell or cells, but does not contact basal surface of the cell or cells.

13. The method of claim 1, wherein the detecting or determining is by means of optical microscopy.

14. The method of claim 13, wherein the optical microscopy is wide field fluorescence imaging microscopy, laser scanning confocal microscopy, multiphoton confocal laser scanning microscopy, multiphoton fluorescence intensity microscopy, or multiphoton fluorescence lifetime imaging microscopy.

15. The method of claim 1, wherein the one or more test stimuli are sweet, sour, salty, bitter and/or umami.

16. The method of claim 1, wherein the one or more test stimuli is an agonist or antagonist.

17. A method for determining a functional cellular response of an isolated taste cell or taste cells from an animal to one or more test stimuli comprising:

a) isolating a lingual epithelium containing intact taste-buds in an intact papilla wherein said lingual epithelium comprises a detectable moiety to one or more test stimuli, wherein said lingual epithelium has a basolateral surface and an apical surface;
b) mounting said lingual epithelium in a chamber to allow separate solutions to independently perfuse said basolateral and apical surfaces of said lingual epithelium;
c) perfusing said basolateral surface with a first solution and said apical surface with a second different solution;
d) contacting said apical surface with a stimuli through said first solution;
e) quantitatively determining a change of said detectable moiety to at least one functional cellular response from said lingual epithelium initiated by said stimuli.

18. The method of claim 17, wherein the detectable moiety is detectable by spectroscopic, photochemical, biochemical, immunochemical, physical, or chemical means.

19. The method of claim 17, wherein the detectable moiety is a fluorescent dye, an electron-dense reagent, an enzyme, biotin, digoxigenin, or a hapten or a protein that has been made detectable.

20. The method of claim 17, wherein the detectable moiety is a calcium-sensitive dye.

21. The method of claim 20, wherein the calcium-sensitive dye is Calcium Green.

22. The method of claim 17, wherein the detectable moiety is a voltage-sensitive dye.

23. The method of claim 17, wherein the taste-bud containing lingual epithelium is obtained from a eukaryotic organism.

24. The method of claim 23, wherein the eukaryotic organism is a mammal.

25. The method of claim 24, wherein the mammal is a rat, mouse, cat, cow, dog, pig, rabbit, chimpanzee, or human.

26. The method of claim 24, wherein the mammal is a pig.

27. The method of claim 17, wherein the taste cell or cells have an apical surface and a basal surface, wherein the stimuli contacts the apical surface of the taste cell or cells, but does not contact basal surface of the cell or cells.

28. The method of claim 17, wherein the detecting or determining is by means of optical microscopy.

29. The method of claim 28, wherein the optical microscopy is wide field fluorescence imaging microscopy, laser scanning confocal microscopy, multiphoton confocal laser scanning microscopy, multiphoton fluorescence intensity microscopy, or multiphoton fluorescence lifetime imaging microscopy.

30. The method of claim 17, wherein the one or more test stimuli are sweet, sour, salty, bitter and/or umami.

31. The method of claim 20, wherein the one or more test stimuli is an agonist or antagonist.

32. A method of identifying one or more test stimuli that affects taste, comprising:
a) isolating a lingual epithelium containing intact taste-buds in an intact papilla wherein said lingual epithelium comprises a detectable moiety to one or more test stimuli, wherein said lingual epithelium has a basolateral surface and an apical surface;
b) mounting said lingual epithelium in a chamber to allow separate solutions to independently perfuse said basolateral and apical surfaces of said lingual epithelium;
c) perfusing said basolateral surface with a first solution and said apical surface with a second different solution;
d) contacting said apical surface with a stimuli through said first solution;
e) quantitatively determining a change of said detectable moiety to at least one functional cellular response from said lingual epithelium initiated by said stimuli.

33. The method of claim 32, further comprising comparing the response of the taste-bud containing lingual epithelium to the one or more test stimuli to the response of the taste-bud containing lingual epithelium to one or more control stimuli.

34. The method of claim 33, wherein the detectable moiety is detectable by spectroscopic, photochemical, biochemical, immunochemical, physical, or chemical means.

35. The method of claim 33, wherein the detectable moiety is a fluorescent dye, an electron-dense reagent, an enzyme, biotin, digoxigenin, or a hapten or a protein that has been made detectable.

36. The method of claim 33, wherein the detectable moiety is a calcium-sensitive dye.

37. The method of claim 36, wherein the calcium-sensitive dye is Calcium Green.

38. The method of claim 33, wherein the detectable moiety is a voltage-sensitive dye.

39. The method of claim 32, wherein the taste-bud containing lingual epithelium is obtained from a eukaryotic organism.

40. The method of claim 39, wherein the eukaryotic organism is a mammal.

41. The method of claim 40, wherein the mammal is a rat, mouse, cat, cow, dog, pig, rabbit, chimpanzee, or human.

42. The method of claim 40, wherein the mammal is a pig.

43. The method of claim 32, wherein the taste cell or cells have an apical surface and a basal surface, wherein the stimuli contacts the apical surface of the taste cell or cells, but does not contact basal surface of the cell or cells.

44. The method of claim 32, wherein the detecting or determining is by means of optical microscopy.

45. The method of claim 44, wherein the optical microscopy is wide field fluorescence imaging microscopy, laser scanning confocal microscopy, multiphoton confocal laser scanning microscopy, multiphoton fluorescence intensity microscopy, or multiphoton fluorescence lifetime imaging microscopy.

46. The method of claim 32, wherein the one or more test stimuli and/or one or more control stimuli are sweet, sour, salty, bitter and/or umami.

47. The method of claim 32, wherein the one or more test stimuli and/or one or more control stimuli is an agonist or antagonist.

48. The method of claim 9, wherein the mammal is a human.

49. The method of claim 24, wherein the mammal is a human.

50. The method of claim 40, wherein the mammal is a human.

* * * * *